US007648993B2

(12) United States Patent
Bear et al.

(10) Patent No.: US 7,648,993 B2
(45) Date of Patent: *Jan. 19, 2010

(54) METHODS OF TREATING DISORDERS WITH GROUP I MGLUR ANTAGONISTS

(75) Inventors: Mark F. Bear, Bristol, RI (US); Kimberly M. Huber, Dallas, TX (US); Stephen T. Warren, Atlanta, GA (US)

(73) Assignees: Brown University, Providence, RI (US); Emory University, Atlanta, GA (US)

(*) Notice: Subject to any disclaimer, the term of this patent is extended or adjusted under 35 U.S.C. 154(b) by 638 days.

This patent is subject to a terminal disclaimer.

(21) Appl. No.: 11/015,328

(22) Filed: Dec. 17, 2004

(65) Prior Publication Data

US 2005/0171067 A1 Aug. 4, 2005

Related U.S. Application Data

(63) Continuation of application No. 10/408,771, filed on Apr. 4, 2003, now Pat. No. 6,916,821, which is a continuation-in-part of application No. 10/114,433, filed on Apr. 2, 2002, now Pat. No. 6,890,931, and a continuation-in-part of application No. PCT/US02/10211, filed on Apr. 2, 2002.

(60) Provisional application No. 60/280,915, filed on Apr. 2, 2001.

(51) Int. Cl.
*A61K 31/435* (2006.01)
*A61K 31/33* (2006.01)

(52) U.S. Cl. ...................................... 514/277; 514/183
(58) Field of Classification Search ........................ None
See application file for complete search history.

(56) References Cited

U.S. PATENT DOCUMENTS

| 6,143,504 | A | * | 11/2000 | Das et al. ................. | 435/6 |
| 6,916,821 | B2 | * | 7/2005 | Bear et al. ................ | 514/277 |
| 2006/0264381 | A1 | * | 11/2006 | Bear ......................... | 514/19 |

FOREIGN PATENT DOCUMENTS

| WO | WO 00/24395 | 5/2000 |
| WO | WO 00/62771 | 10/2000 |
| WO | WO 01/02342 A1 | 1/2001 |
| WO | WO 01/10846 A2 | 2/2001 |
| WO | WO 01/12627 A1 | 2/2001 |
| WO | WO 01/14390 A2 | 3/2001 |

OTHER PUBLICATIONS

Spooren et al. (JPET 2000 vol. 295: 1267-1275).*
Pepeu, G., "Memory Disorders: Novel Treatments, Clinical Perspective," *Life Sciences.* 55(25/26):2189-2194 (1994).
Bartus, R. T., "Drugs to Treat Age-Related Neurodegenerative Problems: The Final Frontier of Medical Science?" *J. Am. Geriatr. Soc.* 38(6):680-695 (1990).
Bordi, F., et al., "Group I Metabotropic Glutamate Receptors: Implications for Brain Diseases", *Prog. Neurobiol.*, 59(1):55-79 (1999).
Knöpfel, T., et al., "Metabotropic Glutamate Receptors: Novel Targets for Drug Development", *J. Med. Chem.*, 38(9):1417-1426 (1995).
Oka A., et al., "The Up-regulation of Metabotropic Glutamate Receptor 5 (mGluR5) in Down's Syndrome Brains," *Acta Neuropathol.*, 97(3):275-278 (1999).
Greenough, W.T., et al., "Synaptic Regulation of Protein Synthesis and the Fragile X Protein," *Proc. Natl. Acad. Sci. USA*, 98(13):7101-7106 (2001).
Grauer, S.M., et al., "Intracerebral Administration of Metabotropic Glutamate Receptor Agonists Disrupts Prepulse Inhibition of Acoustic Startle in Sprague-Dawley Rats," *Psychopharmacology*, 141:405-412 (1999).
Snyder, E.M., et al., "Internalization of Ionotropic Glutamate Receptors in Response to mGluR Activation," *Nature Neurosci.*, 4(11):1079-1085 (2001).
Huber, K.M., et al., "Role for Rapid Dendritic Protein Synthesis in Hippocampal mGluR-Dependent Long-Term Depression," *Science* 288:1254-1256 (2000).
Spooren, W.P.J.M., et al., "Novel Allosteric Antagonists Shed Light on mglu$_5$ Receptors and CNS Disorders," *Trends in Pharmacological Sciences* 22(7):331-337 (2001).
Weiler, I.J., et al., "Fragile X mental retardation protein is translated near synapses in response to neurotransmitter activation," Proc. Natl. Acad.Sci., vol. 94, pp. 5395-5400, May 1997.
O'Leary, D.M. et al., "Selective mGluR5 antagonists MPEP and SIB-1893 decrease NMDA or glutamate-meditated neuronal toxicity through actions that reflect NMDA antagonism,", British Journal of Pharmacology, 131, pp. 1429-1437, 2000.
Varney, M.A. et al., "SIB-1757 and SIB-1893: Selective, Noncompetitive Antagonists of Metabotropic Glutamate Receptor Type 5", Journal of Pharmacology and Experimental Therapeutics, vol. 290, No. 1, pp. 170-181, 1999.

* cited by examiner

*Primary Examiner*—Ardn Marschel
*Assistant Examiner*—Amy A Lewis
(74) *Attorney, Agent, or Firm*—Hamilton, Brook, Smith & Reynolds, P.C.

(57) ABSTRACT mGluR5 antagonists are used for the treatment and prevention of disorders, including Fragile X, autism, mental retardation, schizophrenia and Down's Syndrome. The methods of the invention can be used to treat epilepsy and anxiety in a human having Fragile X syndrome, autism, mental retardation, schizophrenia and Down's Syndrome.

48 Claims, 13 Drawing Sheets

METHODS OF TREATING DISORDERS WITH GROUP I MGLUR ANTAGONISTS

RELATED APPLICATIONS

This application is a continuation of U.S. application Ser. No. 10/408,771, filed Apr. 4, 2003, now U.S. Pat. No. 6,916,821, which is a continuation-in-part of U.S. application Ser. No. 10/114,433, filed Apr. 2, 2002 now U.S. Pat. No. 6,890,931, and a continuation-in-part of International Application No. PCT/US02/10211, which designated the United States and was filed Apr. 2, 2002, published in English, both of which claim the benefit of U.S. Application No. 60/280,915, filed Apr. 2, 2001. The teachings of the above applications are incorporated herein by reference in their entirety.

BACKGROUND OF THE INVENTION

In the mammalian central nervous system (CNS), the transmission of nerve impulses is controlled by the interaction between a neurotransmitter released by a sending neuron and a surface receptor on a receiving neuron, causing excitation of this receiving neuron. L-Glutamate, the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, Annual Reviews in Pharmacology and Toxicology, 21:165 (1981); Monaghan, Bridges, and Cotman, Annual Reviews in Pharmacology and Toxicology, 29:365 (1989); Watkins, Krogsgaard-Larsen, and Honore, Transactions in Pharmaceutical Science, 11:25 (1990).

Excitatory amino acid receptors are classified into two general types. Receptors that are directly coupled to the opening of cation channels in the cell membrane of the neurons are termed "ionotropic." This type of receptor has been subdivided into at least three classes, which are defined by the depolarizing actions of the selective agonists N-methyl-D-aspartate (NMDA), α-amino-3-hydroxy-5-methylisoxazole-4-propionic acid (AMPA), and kainic acid (KA). Five kainate receptors, classified as either high affinity (KA1 and KA2) or low affinity (GluR5, GluR6 and GluR7) kainate receptors have been identified. (Bleakman et al, Molecular Pharmacology, 1996, Vol. 49, No. 4, pp. 581-585).

The second general type of receptor is the G-protein or second messenger-linked "metabotropic" excitatory amino acid receptor. This second type is a highly heterogeneous family of glutamate receptors that are linked to multiple second messenger systems. Based on their amino acid sequence homology, agonist pharmacology, and coupling to transduction mechanisms, the 8 presently known mGluR sub-types are classified into three groups. Group I receptors (mGluR1 and mGluR5) have been shown to be coupled to stimulation of phospholipase C resulting in phosphoinositide hydrolysis and elevation of intracellular $Ca^{++}$ levels, and, in some expression systems, to modulation of ion channels, such as $K^+$ channels, $Ca^{++}$ channels, non-selective cation channels, or NMDA receptors. Group II receptors (mGluR2 and mGluR3) and Group III receptors (mGluRs 4, 6, 7, and 8) are negatively coupled to adenylcyclase and have been shown to couple to inhibition of cAMP formation when heterologously expressed in mammalian cells, and to G-protein-activated inward rectifying potassium channels in Xenopus oocytes and in unipolar brush cells in the cerebellum. Besides mGluR6, which is essentially only expressed in the retina, the mGluRs are felt to be widely expressed throughout the central nervous system.

Both types of receptors appear not only to mediate normal synaptic transmission along excitatory pathways, but also participate in the modification of synaptic connections during development and throughout life. Schoepp, Bockaert, and Sladeczek, Trends in Pharmacological Science, 11:508 (1990); McDonald and Johnson, Brain Research Reviews, 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. Agonists and antagonists of these receptors may be useful for the treatment of acute and chronic neurodegenerative conditions.

BRIEF SUMMARY OF THE INVENTION

The present invention provides a method of treating or preventing disorders, including but not limited to Fragile X syndrome, Down's Syndrome, and other forms of mental retardation, schizophrenia, and autism, comprising administering to a patient (e.g., a human) an antagonist of Group I mGluR (mGluR1 or mGluR5). In a particular embodiment, the mGluR antagonist is selective for mGluR5, e.g., in the hippocampus.

The present invention provides:
a) the use of an mGluR antagonist for the treatment of Down's Syndrome, Fragile X and other forms of mental retardation, schizophrenia and autism,
b) the use of an mGluR antagonist in the manufacture of a pharmaceutical composition for the treatment of Down's Syndrome, Fragile X and other forms of mental retardation, schizophrenia and autism,
c) a method of treating Down's Syndrome, Fragile X and autism in a subject in need of such treatment, comprising administration to such subject of a therapeutically effective amount of an mGluR antagonist, and
d) a method of treating Down's Syndrome, Fragile X and other forms of mental retardation, schizophrenia and autism in a subject in need of such treatment, comprising administration to such subject of a therapeutically effective amount of a pharmaceutical composition comprising an mGluR antagonist.

Certain embodiments of the invention relate to a method for treating Down's Syndrome, Fragile X and other forms of mental retardation, schizophrenia and autism, comprising co-administering other therapeutic agents (e.g., simultaneously or at different times) to the patient (human or other animal) with an amount of an mGluR antagonist sufficient to treat the disorder. In certain embodiments, the composition is for oral administration or for transdermal administration.

In another aspect of the invention, the mGluR antagonist is a selective mGluR5 antagonist. In another aspect of the invention, the mGluR antagonist is selected from 6-methyl-2-(phenylazo)-3-pyridinol, α-methyl-4-carboxyphenylglycine (MCPG), 2-methyl-6-(phenylethynyl)-pyridine (MPEP), 3S,4aR,6S,8aRS-6-((((1H-tetrazole-5-yl)methyl)oxy)methyl)-1,2,3,4,4a,5,6,7,8,8a-decahydroisoquinoline-3-carboxylic acid, 2-methyl-6-[(1E)-2-phenylethynyl]-pyridine, (E)-6-methyl-2-styryl-pyridine (SIB 1893), LY293558, 6-(((4-carboxy)phenyl)methyl)-1,2,3,4,4a,5,6,7,8,8a-decahydroisoquinoline-3-carboxylic acid, 3 S,4aR,6S,8aR-6-((((1H-tetrazole-5-yl)methyl)oxy)methyl)-1,2,3,4,4a,5,6,7,8,8a-decahydroisoquinoline-3-carboxylic acid, and 3S,4aR,6S,8aR-6-(((4-carboxy)-phenyl)methyl)-1,2,3,4,4a,5,6,7,8,8a-decahydroisoquinoline-3-carboxylic acid, and their pharmaceutically acceptable salts, analogues and derivatives thereof. In other aspects, the mGluR5 receptor antagonist is formulated with a pharmaceutically acceptable diluent or carrier.

Another aspect of the invention is a kit comprising one or more mGluR antagonists, provided in single oral dosage form or as a transdermal patch, in an amount sufficient for treating neurological disorders selected from Fragile X, Down's Syndrome, and other forms of mental retardation, autism, and schizophrenia in a patient, and in association with instructions (written and/or pictorial) describing the use of the kit for treating neurological disorders, and optionally, warnings of possible side effects and drug-drug or drug-food interactions.

One aspect of the present invention is a method for conducting a pharmaceutical business. Accordingly, one embodiment of the present invention is a method for conducting a pharmaceutical business, comprising:

a. manufacturing a kit comprising one or more mGluR antagonists, provided in single oral dosage form or as a transdermal patch, in an amount sufficient for treating neurological disorders selected from Fragile X, Down's Syndrome and other forms of mental retardation, autism, and schizophrenia in a patient, and in association with instructions (written and/or pictorial) describing the use of the kit for treating neurological disorders, and optionally, warnings of possible side effects and drug-drug or drug-food interactions; and b. marketing to healthcare providers the benefits of using the kit to treat neurological disorders of patients.

Another embodiment of the present invention is a method for conducting a pharmaceutical business, comprising:

a. providing a distribution network for selling a kit comprising one or more mGluR5 antagonists, provided in single oral dosage form or as a transdermal patch, in an amount sufficient for treating neurological disorders selected from Fragile X, Down's Syndrome and other forms of mental retardation, autism, and schizophrenia in a patient, and in association with instructions (written and/or pictorial) describing the use of the kit for treating neurological disorders, and optionally, warnings of possible side effects and drug-drug or drug-food interactions; and b. providing instruction material to patients or physicians for using the kit to treat neurological disorders of patients.

Another embodiment of the present invention is a method for conducting a pharmaceutical business, comprising:

a. determining an appropriate dosage of an mGluR antagonist to treat neurological disorders in a class of patients;

b. conducting therapeutic profiling of one or more formulations of the mGluR5 antagonist identified in step (a), for efficacy and toxicity in animals; and c. providing a distribution network for selling a the formulations identified in step (b) as having an acceptable therapeutic profile.

In certain embodiments, the invention provides a method which includes an additional step of providing a sales group for marketing the preparation to healthcare providers.

Further still, the present invention discloses a method for conducting a pharmaceutical business, comprising:

a. determining an appropriate dosage of an mGluR antagonist to treat a neurological disorder in a class of patients; and b. licensing, to a third party, the rights for further development and sale of the mGluR5 antagonist for treating the neurological disorder.

In yet another aspect, the invention relates to a method for preparing a pharmaceutical preparation, comprising combining an mGluR antagonist and a pharmaceutically acceptable excipient in a composition for simultaneous administration of the drug.

In still another aspect, the invention relates to a method for conducting a pharmaceutical business, by manufacturing a preparation of an mGluR antagonist (or prodrug or metabolite thereof) or a kit including separate formulations of each, and marketing to healthcare providers the benefits of using the preparation or kit in the treatment of Down's Syndrome, Fragile X and other forms of mental retardation, autism, and schizophrenia.

In yet another aspect, the invention provides a method for conducting a pharmaceutical business, by providing a distribution network for selling the combinatorial preparations and kits, and providing instruction material to patients or physicians for using such preparation to treat Down's Syndrome, Fragile X and other forms of mental retardation, autism, and schizophrenia.

In still a further aspect, the invention relates to a method for conducting a pharmaceutical business, by determining an appropriate formulation and dosage of an mGluR antagonist. In certain embodiments, the method further includes an additional step of providing a sales group for marketing the preparation to healthcare providers.

In yet another aspect, the invention provides a method for conducting a pharmaceutical business by determining an appropriate formulation and dosage of an mGluR antagonist, and licensing, to a third party, the rights for further development and sale of the formulation. In another aspect, the class of patients suffers from neurological disorders.

In other embodiments, the method comprises administering to the patient an effective amount of the mGluR antagonist or combinations thereof. In another embodiment, the mGluR antagonist is administered in a dose ranging from about 10 to about 1000 mg/kg body weight/day. In one embodiment, the mGluR antagonist is administered in a dose ranging from about 50 to about 800 mg/kg body weight/day. In another embodiment, the mGluR antagonist is administered in a dose ranging from about 250 to about 500 mg/kg body weight/day.

In certain embodiments, the mGluR antagonist has an $ED_{50}$ of 10 µM, 1 µM, 100 nm, 10 nm, or less. In one embodiment, the TI is 10, 100, 1000, or greater. In certain embodiments, the $ED_{50}$ for group I receptor antagonism is at least 10 times less than the $ED_{50}$ for each of group II or group III receptor antagonism, e.g., mGluR2, mGluR3, mGluR4, mGluR6, mGluR7, and mGluR8. The methods of the invention can be used to treat neurological conditions (e.g., Fragile X syndrome, mental retardation).

In yet another embodiment, the invention is directed to a method of treating anxiety in a human having Fragile X syndrome, comprising the step of administering to the human a Group I mGluR antagonist.

In still another embodiment, the invention is a method of treating an epilepsy in a human having Fragile X syndrome, comprising the step of administering to the human a Group I mGluR antagonist.

An additional embodiment of the invention is a method of treating anxiety in a human having a disorder selected from the group consisting of autism, mental retardation and Down's Syndrome, comprising the step of administering to the human a Group I mGluR antagonist.

In another embodiment, the invention is a method of treating an epilepsy in a human having a disorder selected from the group consisting of autism, mental retardation and Down's Syndrome, comprising the step of administering to the human a Group I mGluR antagonist.

In still another embodiment, the invention is a method of treating a subject, comprising the step of administering a Group I mGluR antagonist to a subject having autism.

In another embodiment, the invention is a method of treating a subject, comprising the step of administering an mGluR5 antagonist to a subject having autism.

In an additional embodiment, the invention is a method of treating a subject, comprising the step of administering an effective amount of a Group I mGluR antagonist to a subject having autism, wherein the Group I mGluR antagonist is selected from the group consisting of (E)-6-methyl-2-styryl-pyridine (SIB 1893), 6-methyl-2-(phenylazo)-3-pyridinol, α-methyl-4-carboxyphenylglycine (MCPG) and 2-methyl-6-(phenylethynyl)-pyridine (MPEP).

In yet another embodiment, the invention is a method of treating a subject comprising the step of administering an effective amount of a Group I mGluR antagonist to a subject having autism and fragile X syndrome.

Treatment of humans with Group I mGluR antagonists can halt, diminish, inhibit, reverse or ameliorate conditions associated with mental retardation (e.g., anxiety, epilepsy, autism and Fragile X), thereby increasing the quality of life for humans afflicted with mental retardation conditions.

DETAILED DESCRIPTION OF THE FIGURES

FIG. 1 shows (RS)-3,5-dihydroxyphenylglycine (DHPG)-induced long-term depression (LTD).

FIG. 1A depicts the dose dependent effects of DHPG application (5 min; indicated by the downward arrow) on field potential (FP) slope values (10 µM DHPG; n=5; 50 µM; n=11; 100 µM DHPG; n=4). Inset: schematic of placement of stimulating (S) and extracellular recording (R) electrodes in an isolated CA1 hippocampal slice. Representative field potentials (2-min average) from a slice treated with 50 µM DHPG and taken at the times indicated by the numbers on the graph. Calibration: 0.5 mV, 5 ms.

FIG. 1B shows that DHPG-LTD is stimulation independent. Inset: placement of stimulating electrodes (S1 and S2) that stimulated 2 independent inputs in alternation. Stimulation to 1 pathway (OFF path; ○) was turned off immediately prior to DHPG application and resumed 30 min after DHPG wash out, while the other (ON path; ●) input was stimulated at baseline frequency (0.067 Hz) for the duration of the experiment. A similar magnitude of depression was observed in both the ON and OFF paths (n=4).

FIG. 1C shows that DHPG-LTD is saturable. Two applications of DHPG are sufficient to saturate LTD. A 3rd DHPG application did not induce any further depression (n=8).

FIG. 1D shows that DHPG (50 µM; 5 min) application induces a persistent depression of average excitatory postsynaptic potential (EPSP) slope values (n=6). Representative EPSP waveforms (2-min average) taken from an experiment at times indicated by numbers on the graph. Calibration: 5 mV, 10 ms.

FIG. 1E shows that DHPG (50 µM; 5 min) application decreases excitatory postsynaptic current (EPSC) amplitudes. Cells were voltage clamped at −70 mV. Recording mode was switched from voltage clamp to current (I) clamp during and 5 min after DHPG application as indicated by the bar. Representative EPSCs (2-min average) taken from an experiment at the times indicated by the numbers on the graph. Calibration: 125 pA, 25 ms.

FIG. 2A shows that DHPG-LTD is NMDAR independent. Preincubation of slices in D-2-amino-5-phosphonopentanoic acid (AP5; 50 M; ●; n=5) does not affect the magnitude of DHPG-LTD as compared with interleaved control slices (○; n=4).

Figure 2:
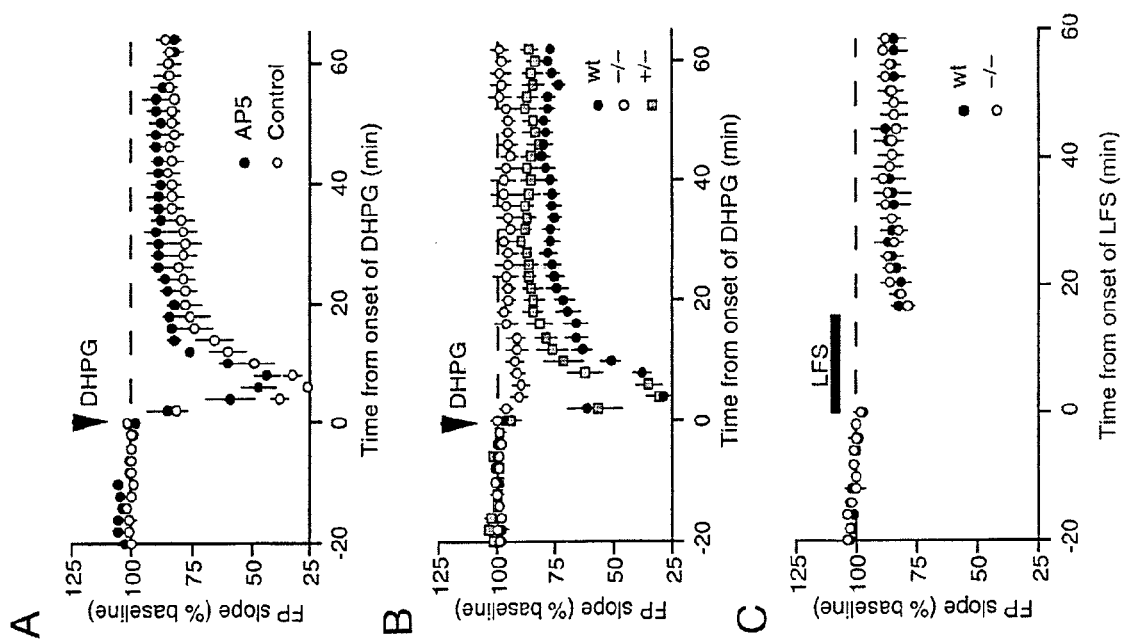
FIG. 2 shows that DHPG-LTD, but not N-methyl-D-aspartate receptor (NMDAR)-dependent LTD, require mGluR5.

FIG. 2B shows that DHPG-LTD requires mGluR5. DHPG application to slices from homozygote mGluR5 knockout mice (−/−; ○; n=8) does not induce LTD. Intermediate LTD is observed in heterozygotes (+/−; 0; n=6) as compared with slices from wild-type mice (wt; ●; n=9).

FIG. 2C shows that low-frequency synaptic stimulation (LFS)-induced LTD does not require mGluR5. LFS induces a similar magnitude of LTD in both homozygote knockout mice (−/−; ○; n=6) as compared with wild-type mice (wt, ●; n=6).

Figure 3:
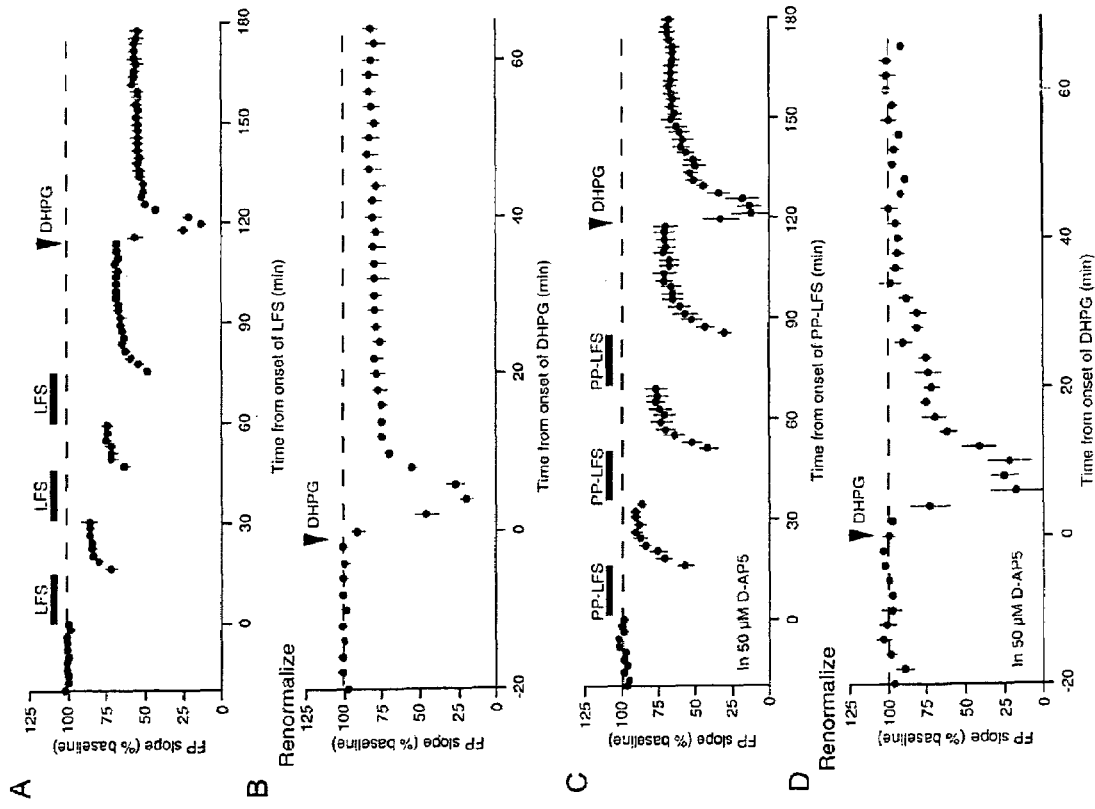

FIG. 3 shows that DHPG-LTD is occluded by mGluR-dependent LTD induced with PP-LFS, but not NMDAR-dependent LTD.

FIG. 3A shows the results of experiments when repeated episodes of LFS were delivered to saturate NMDAR-dependent LTD. DHPG (downward arrow) was then applied to the slice.

FIG. 3B shows renormalized FP slope values to the pre-DHPG baseline (n=8).

FIG. 3C shows the results of experiments when repeated episodes of PP-LFS were delivered to saturate mGluR-dependent LTD. DHPG (downward arrow) was then applied to the slice. The entire experiment was performed in 50 µM D-AP5 to prevent induction of NMDAR-dependent LTD.

FIG. 3D shows renormalized FP slope values to the pre-DHPG baseline (n=5).

Figure 4:
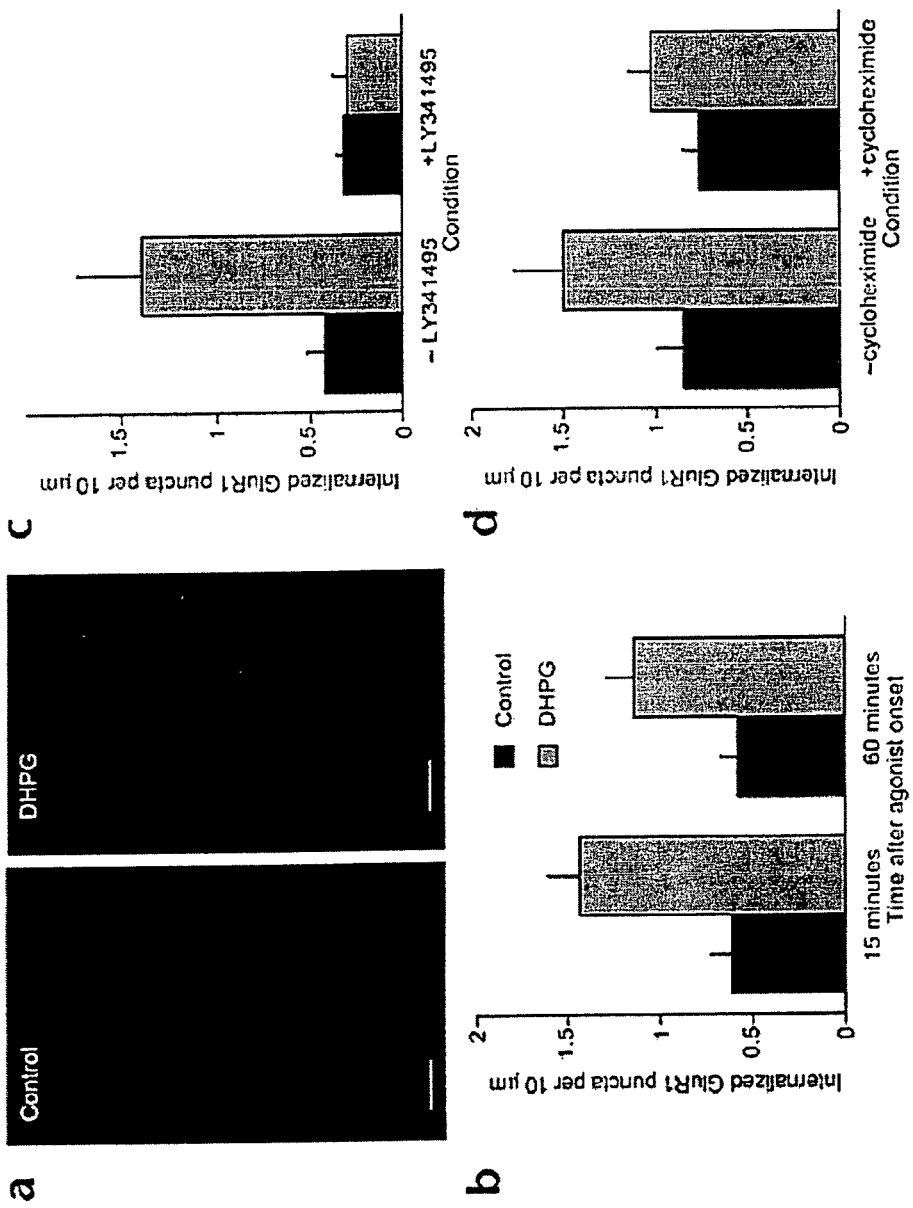

FIG. 4A shows representative images of a control neuron and a neuron 15 minutes after mGluR stimulation labeled via acid strip immunocytochemistry for internalized GluR1. Scale bar, 10 µm.

FIG. 4B shows that quantification revealed a 2.5-fold increase in the density of internalized puncta as early as 15 min, lasting at least 60 min.

FIG. 4C shows that mGluR-stimulated endocytosis of GluR1 is blocked by a Group I mGluR antagonist, LY344545.

FIG. 4D shows that inhibition of protein synthesis by cycloheximide (60 µM) treatment decreases mGluR-stimulated endocytosis.

Figure 5:
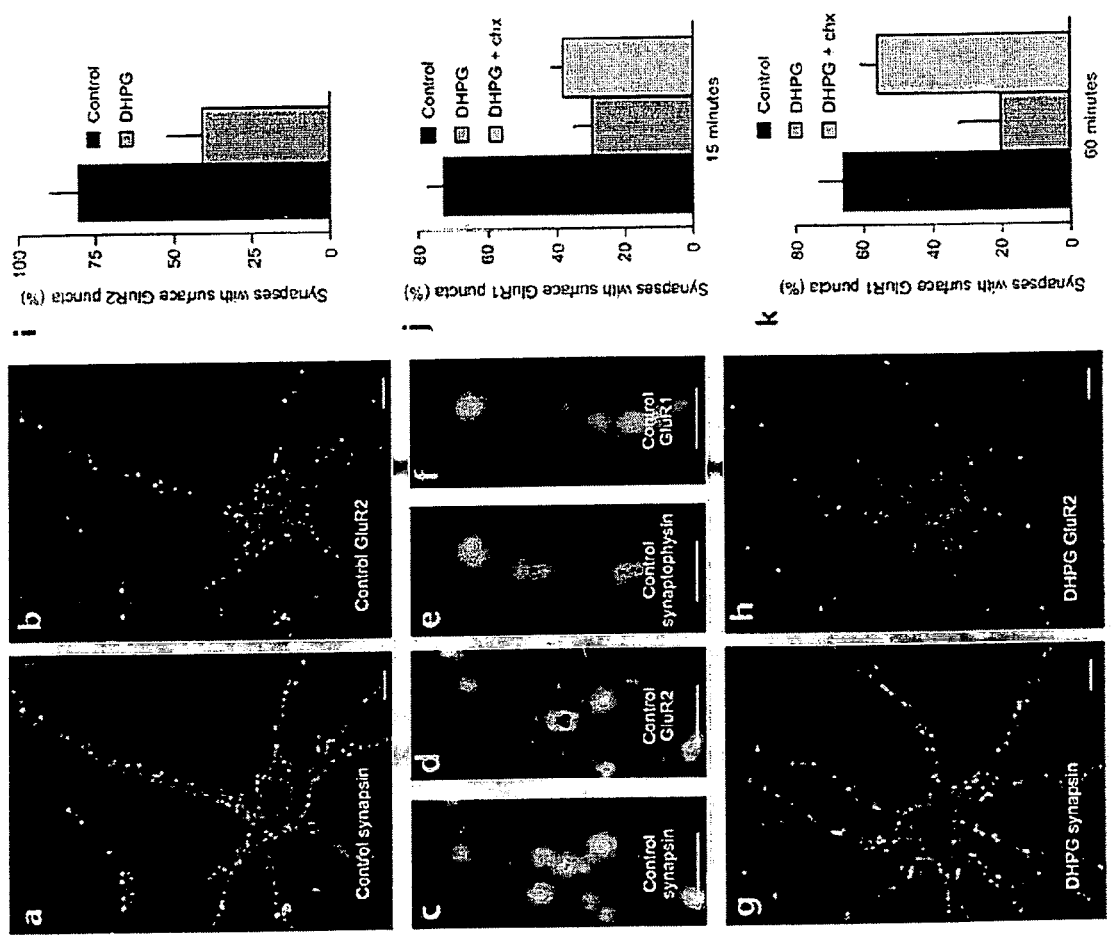

FIGS. 5A and 5B show representative images of a control neuron stained with an antibody directed against the synaptic marker synapsin I (FIG. 5A) and an antibody against the N-terminus of GluR2 (FIG. 5B) Scale bar, 10 µm.

FIGS. 5C and 5D show higher magnification images of the same cell as in FIG. 5A demonstrating the colocalization of synapsin (FIG. 5C) and GluR2 (FIG. 5D) Scale bar, 5 µm.

FIGS. 5E and 5F depict a similar degree of colocalization was observed with antibodies against synaptophysin (FIG. 5E) and the N-terminus of GluR1 (FIG. 5F).

FIGS. 5G and 5H show that no change in synapsin puncta density was detected 1 h after DHPG (FIG. 5G) but there was a large decrease in the number of synaptic GluR2 puncta (FIG. 5H) Scale bar, 10 µm.

FIG. 5I show that 80.6±9.0% of synapsin puncta colocalized with GluR2 on control neurons. However, 1 h following DHPG, only 40.8±11% of synapses had surface staining for GluR2.

FIGS. 5J and 5K show that GluR1-positive synapses are reduced by DHPG treatment and the stable expression of this change is inhibited by cycloheximide. Only 29.3±5.4% of synaptophysin-positive synapses expressed GluR1 puncta 15 min after DHPG compared to 72.5±4.7% in control cultures. This effect of DHPG was not affected by cycloheximide (FIG. 5J). In contrast, cycloheximide significantly inhibited the loss of GluR1 measured 60 min following DHPG (FIG. 5K).

FIG. 6A shows a representative blot of samples of total and biotinylated surface GluR1 from a control culture (lanes 1 and 2) and 60 min following DHPG treatment (lanes 3 and 4).

FIG. 6B depicts densitometric quantification 60 min following DHPG. Surface GluR1 levels were reduced to 56.8±4.0% of control levels.

FIG. 7A shows representative mEPSC recordings from a cell before and one hour after DHPG application.

FIG. 7B depicts cumulative probability histograms for inter-event interval and amplitude for the cell depicted in FIG. 7A before DHPG and in a period beginning 45 min after DHPG application.

FIG. 7C depicts group-averaged mEPSC amplitude and inter-event interval before, 15 min and 1 h following DHPG application.

Figure 8:
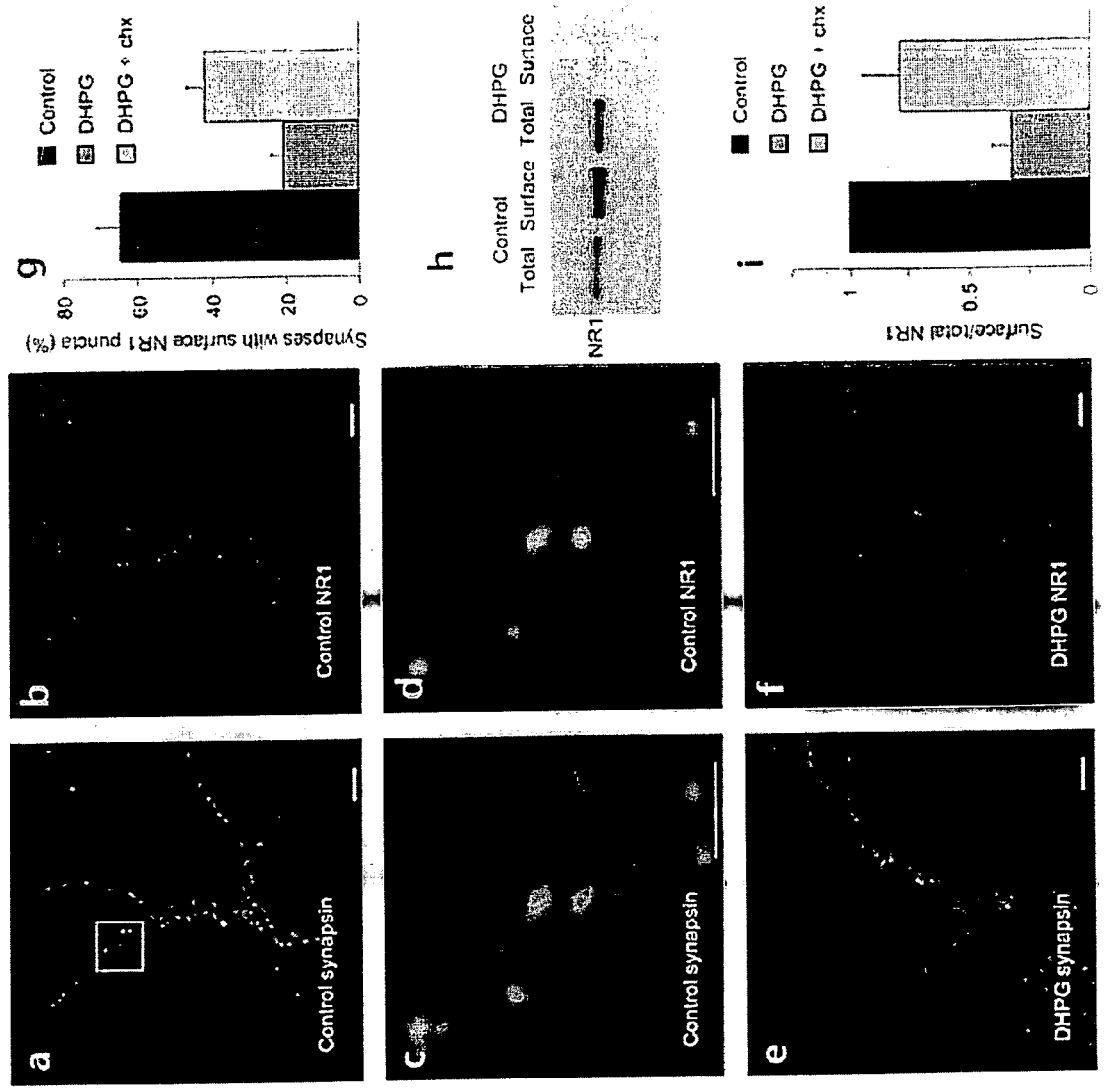

FIGS. 8A and 8B show representative images of a control neuron stained with an antibody directed against the synaptic marker synapsin I (FIG. 8A) and an antibody to the N-terminus of NR1 (FIG. 8B). Scale bar, 10 µm.

FIGS. 8C and 8D depict higher magnification images of the same cell as in FIG. 8A demonstrating the colocalization of synapsin (FIG. 8C) and NR1 (FIG. 8D). Scale bar, 5 µm.

FIGS. 8E and 8F show that no change in synapsin puncta density was detected 1 h after DHPG (FIG. 8E) but there was a large decrease in the number of synaptic NR1 puncta (FIG. 8F). Scale bar, 10 µm.

FIG. 8G shows that DHPG reduced the percent of synapses positive for NR1 60 min after treatment onset and that this effect was inhibited by cycloheximide.

FIG. 8H shows a representative blot of total and biotinylated surface NR1 in control (lanes 1 and 2) and 60 minutes following treatment with DHPG (lanes 3 and 4; reprobe of blot in FIG. 3A).

FIG. 8I shows that after sixty minutes of DHPG treatment, surface NR1 levels were reduced to 32.3±8.2% of control levels. Cycloheximide reduced the loss of surface NMDARs to 79.1±14.5% of control levels.

Figure 9:
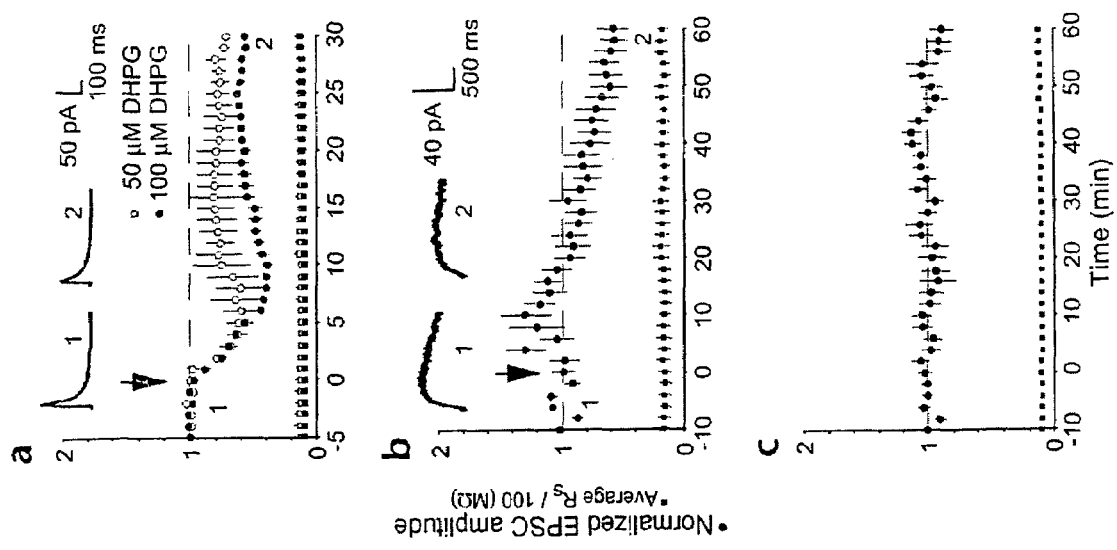

FIGS. 9A, 9B and 9C shows that DHPG application attenuates synaptically evoked NMDAR-mediated EPSCs and NMDA-evoked currents. DHPG-induced depression of synaptically evoked NMDAR EPSCs. Arrows indicate onset of 5 min DHPG application. $R_s$, series resistance.

FIG. 9B shows a two-minute average of NMDA-evoked current amplitudes before and after application of 100 µM DHPG.

FIG. 9C shows a two-minute average of control NMDA-evoked currents.

Figure 10A:
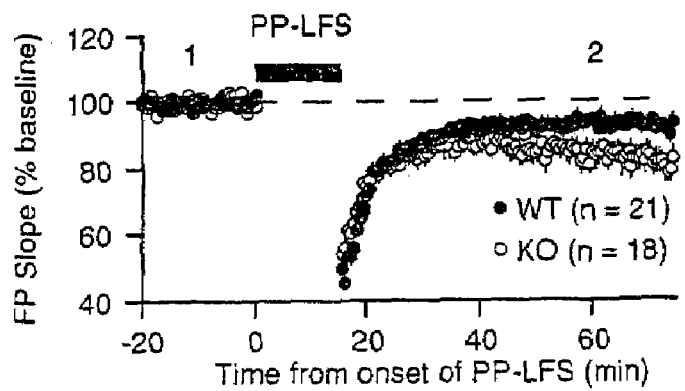
Figure 10B:
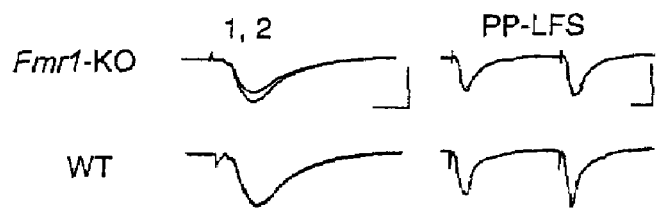
Figure 10C:
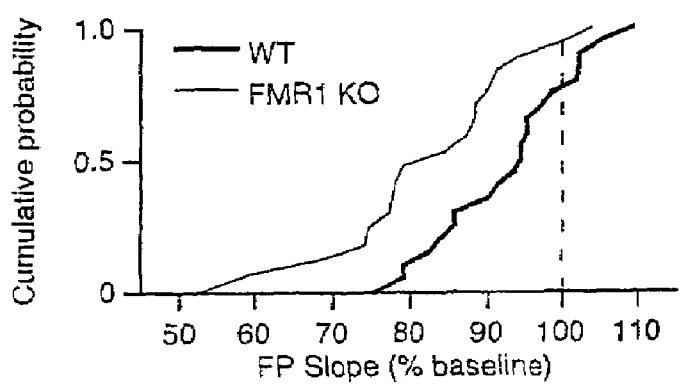

FIGS. 10A, 10B and 10C show that the synaptic induction of mGluR-LTD (paired-pulse low-frequency stimulation (PP-LFS)) is significantly enhanced in the hippocampus of Fragile X mental retardation Fmr1-KO (knock out) mice compared with WT (wild type) controls.

Figure 11A:
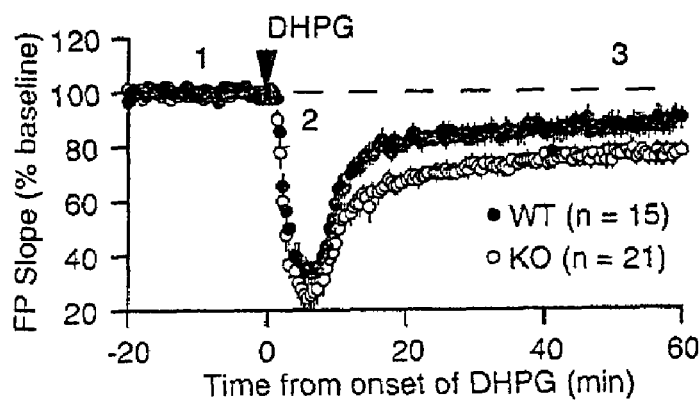
Figure 11B:
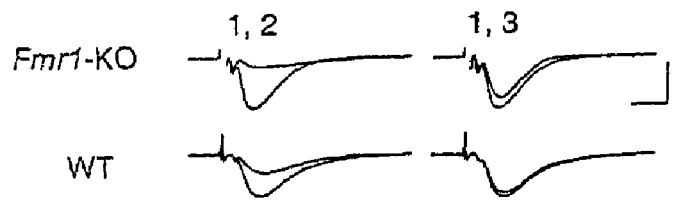
Figure 11C:
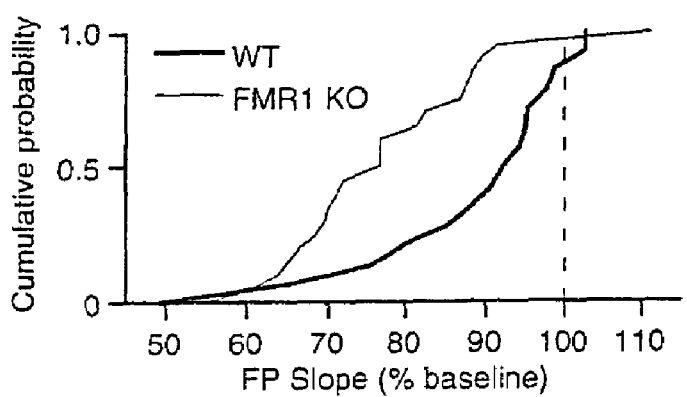

FIGS. 11A, 11B and 11C show that the mGluR agonist DHPG (5 min; 100 µM) induces a greater LTD of synaptic responses in the hippocampus of Fmr1-KO mice as compared to wild-type (WT) littermate controls.

Figure 12A:
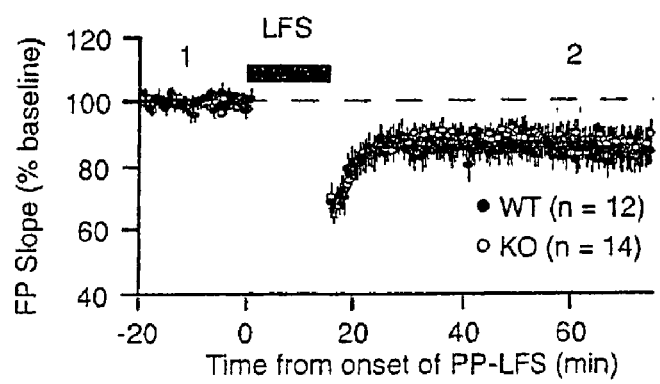
Figure 12B:
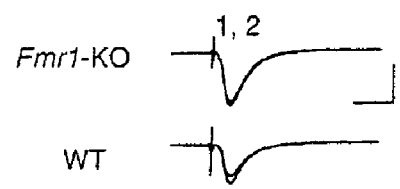
Figure 12C:
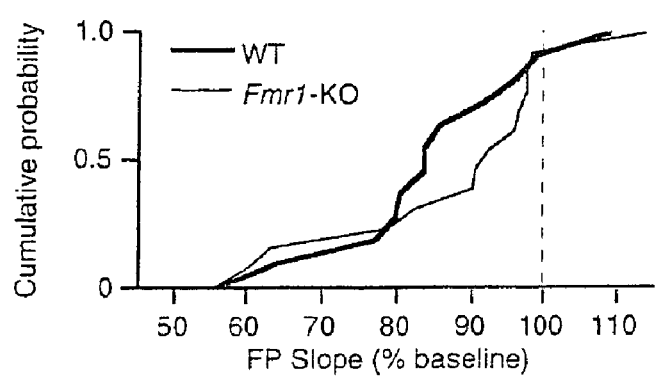

FIGS. 12A, 12B and 12C show that the synaptic induction of NMDAR-dependent LTD is comparable in Fmr1-KO mice and WT controls.

Figure 13:
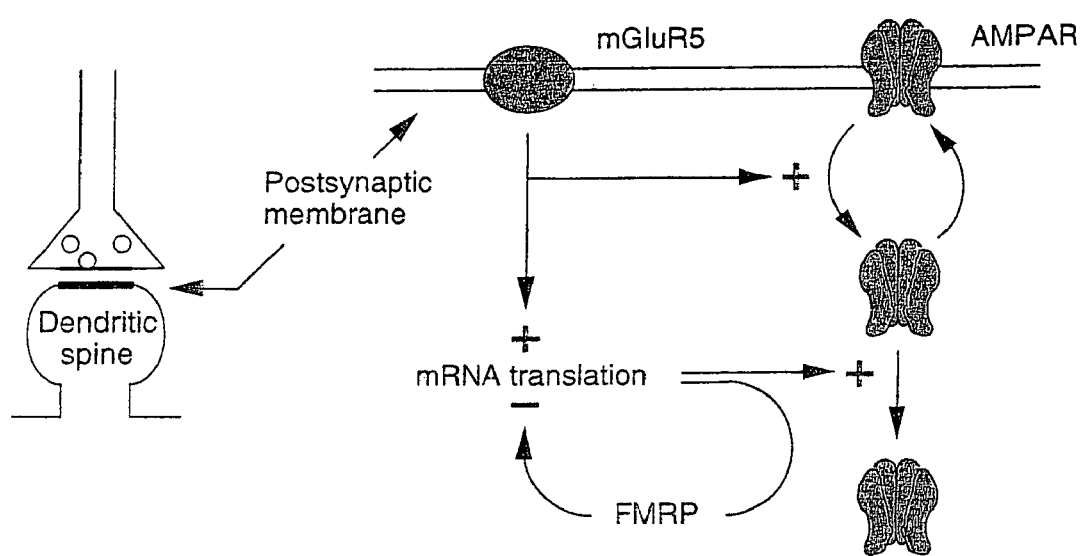

FIG. 13 depicts a model of the relation between Group I mGluR (e.g., mGluR5) and FMRP. AMPAR is α-amino-3-hydroxy-5-methyl-4-isoxazolepropionic acid receptor.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown b way of illustration and not as limitations of the invention. The principle features of this invention can be employed in various embodiments without departing from the scope of the invention.

Evidence that Fragile X mental retardation protein (FMRP) is involved in activity-dependent local synaptic protein synthesis has only recently emerged. The major excitatory neurotransmitter glutamate, via group I metabotropic glutamate receptors (mGluRs), stimulates protein synthesis in dendrites. The Group I mGluRs are a subgroup of the G-protein coupled mGluR family, and are composed of two subtypes, mGluR1 and mGluR5. Subsequent work demonstrated that FMR1 mRNA is present in dendrites and FMRP is synthesized in response to mGluR activation of synaptoneurosomes (Weiler, et al., 1997). Because FMRP itself can regulate mRNA translation, the synthesis of FMRP at synapses in response of mGluR activation may be a mechanism by which neuronal activity can regulate or control synthesis of other proteins important for synaptic plasticity and development.

Although it was known that mGluR activation can stimulate protein synthesis, and specifically that of FMRP, the functional role of this mechanism was unknown until recently. Several studies have demonstrated that activation of group I mGluRs with either synaptic stimulation or the selective agonist R,S-dihydroxyphenylglycine (DHPG) induces long-term depression (LTD) of synaptic responses in area CA1 of the rat hippocampus (Fitzjohn et al., 1999; Kemp and Bashir, 1999; Huber et al., 2000). LTD is dependent on mGluR5 and most importantly requires the rapid and dendritic synthesis of new proteins (Huber et al., 2000). This LTD mechanism provides clues to the function of glutamate or activity-induced stimulation of local dendritic protein synthesis.

It has been suggested that an LTD-like mechanism could be responsible for elimination or pruning of inappropriate synapses which are formed during early periods of postnatal development (Colman, et al., 1997; Bear and Rittenhouse, 1999). Recent evidence supports this hypothesis. Treatment of hippocampal neuronal cultures with the group I mGluR agonist, DHPG, results in a long-term decrease in the surface expression of AMPA-subtype glutamate receptors (AMPAR), the receptors responsible for synaptic transmission at excitatory synapses. Like LTD, the long-term decrease in the AMPAR surface expression is dependent on protein synthesis (Snyder, et al., 2000). Preliminary data also indicate a concomitant reduction in the number of presynaptic terminals after DHPG treatment. Together, these results indicate that activation of mGluR5 results in decreases in synaptic strength most likely mediated by a reduction or elimination in the number of excitatory synapses. This synapse elimination process may contribute to the formation of appropriate synaptic connections during development as well as in the storage of memories in the adult.

The present invention is based on the discovery that FMRP plays an integral part in the LTD mechanism. As described in detail below, the role of FMRP in LTD was discovered using the FMR1 knockout mouse model of Fragile X syndrome. Briefly, hippocampal brain slices were prepared from either knockout or wildtype littermates. LTD was induced with either DHPG application or a synaptic stimulation protocol, termed paired-pulse low frequency stimulation (PP-LFS). Surprisingly, a significant enhancement of LTD was observed in the knockout mice in both the DHPG and PP-LFS treated slices. These results suggest that FMRP may normally function as an inhibitor of mGluR-dependent protein synthesis and, in the absence of FMRP, there is unregulated synthesis of the proteins required for LTD. One implication of these results is that an excess of LTD or a synapse elimination mechanism in FMR1 knockout mice or Fragile X patients may perturb the normal synaptic development process and lead to abnormalities in dendritic spine structure and eventually to cognitive deficits. Alternatively or in addition, the enhancement of an LTD-like mechanism in the adult could result in the ineffective storage of information in the brain which could also contribute to mental retardation.

The discovery of a neuronal mechanism associated with mental retardation provides therapies to prevent or reverse the synaptic abnormalities and cognitive deficits associated with Fragile X syndrome, Down's syndrome and other forms of mental retardation, autism, schizophrenia and other disorders involving down-regulation of FMRP levels or expression. For example, treatment could be the administration of antagonists of Group I mGluRs, such as mGluR5, during early postnatal development to attenuate the abnormally enhanced LTD and restore the balance of synaptic formation and elimination. Furthermore, treatment of adults with antagonists of Group I mGluRs, such as mGluR5s, may reduce learning deficits in light of evidence that neurons retain their ability to form dendrites and modulate surface expression of receptors for some time.

The present invention relates to the use of antagonists of Group I mGluRs, such as antagonists of mGluR5 and mGluR1, for treating Down's Syndrome, Fragile X and other forms of mental retardation, schizophrenia and autism. An mGluR antagonist is a substance which diminishes or abolishes the effect of a ligand (or agonist) that activates an mGluR. Thus, the antagonist may be, for example, a chemical antagonist, a pharmacokinetic antagonist, an antagonist by receptor block, a non-competitive antagonist, or a physiological antagonist.

Antagonists may act the level of the ligand-receptor interactions, such as by competitively or non-competitively (e.g., allosterically) inhibiting ligand binding. In other embodiments, the antagonist may act downstream of the receptor, such as by inhibiting receptor interaction with a G protein or downstream events associated with G protein activation such as stimulation of phospholipase C, elevation in intracellular calcium, the production of or levels of cAMP or adenylcyclase, stimulation and/or modulation of ion channels (e.g., K+, Ca++). The antagonists can alter, diminish, halt, inhibit or prevent the above-referenced cellular signaling events.

A "pharmacokinetic antagonist" effectively reduces the concentration of the active drug at its site of action, e.g., by increasing the rate of metabolic degradation of the active ligand. Antagonism by receptor-block involves two important mechanisms: 1) reversible competitive antagonism and 2) irreversible, or non-equilibrium, competitive antagonism. Reversible competitive antagonism occurs when the rate of dissociation of the antagonist molecule from the receptor is sufficiently high that, on addition of the ligand, the antagonist molecules binding the receptors are effectively replaced by the ligand. Irreversible or non-equilibrium competitive antagonism occurs when the antagonist dissociates very slowly or not at all from the receptor, with the result that no change in the antagonist occupancy takes place when the ligand is applied. Thus, the antagonism is insurmountable. As used herein, a "competitive antagonist" is a molecule which binds directly to the receptor or ligand in a manner that sterically interferes with the interaction of the ligand with the receptor.

Non-competitive antagonism describes a situation where the antagonist does not compete directly with ligand binding at the receptor, but instead blocks a point in the signal transduction pathway subsequent to receptor activation by the ligand. Physiological antagonism loosely describes the interaction of two substances whose opposing actions in the body tend to cancel each other out. An antagonist can also be a substance that diminishes or abolishes expression of functional mGluR. Thus, an antagonist can be, for example, a substance that diminishes or abolishes: 1) the expression of the gene encoding mGluR5, 2) the translation of mGluR5 RNA, 3) the post-translational modification of mGluR5 protein, or 4) the insertion of GluR5 into the cell membrane.

II. Definitions

An "effective amount" refers to the amount of a compound including an mGluR antagonist that is effective, upon single or multiple dose administration to a patient, in treating the patient suffering from the named disorder.

The term "$ED_{50}$" means the dose of a drug that produces 50% of its maximum response or effect.

The term "$IC_{50}$" means the concentration of a drug which inhibits an activity or property by 50%, e.g., by reducing the frequency of a condition, such as cell death, by 50%, by reducing binding of a competitor peptide to a protein by 50% or by reducing the level of an activity by 50%.

The term "$LD_{50}$" means the dose of a drug that is lethal in 50% of test subjects.

A "patient" or "subject" to be treated by the subject method can mean either a human or non-human animal.

"Composition" indicates a combination of multiple substances into an aggregate mixture.

The term "prodrug" is intended to encompass compounds which, under physiologic conditions, are converted into the therapeutically active agents of the present invention. A common method for making a prodrug is to include selected moieties, such as esters, which are hydrolyzed under physiologic conditions to reveal the desired molecule. In other embodiments, the prodrug is converted by an enzymatic activity of the host animal.

The term "metabolites" refers to active derivatives produced upon introduction of a compound into a biological milieu, such as a patient.

An "agonist" is a molecule which activates a certain type of receptor. For example, glutamate molecules act as agonists when they excite EM receptors. By contrast, an "antagonist" is a molecule which prevents or reduces the effects exerted by an agonist on a receptor. The term "therapeutic index" refers to the therapeutic index (TI) of a drug, defined as $LD_{50}/ED_{50}$.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers drug to the skin, permitting the drug to pass through the skin into the patient's system.

The term "statistically significant" as used herein means that the obtained results are not likely to be due to chance fluctuations at the specified level of probability. The two most commonly specified levels of significance are 0.05 (p=0.05) and 0.01 (p=0.01). The level of significance equal to 0.05 and 0.01 means that the probability of error is 5 out of 100 and 1 out of 100, respectively.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The term "distribution network" refers to individuals or organizations that are linked together and transfer goods from one individual, organization, or location to a plurality of other individuals, organizations, or locations.

The term "sales group" refers to an organization of individuals who are associated with the selling of a certain product.

The term "licensing" refers to the granting of authority by the owner of a patent or the holder of know-how to another, empowering the latter to make or use the patented composition or method or the know-how.

III. Exemplary Compounds of the Invention.

A. Exemplary mGluR Antagonists

The present invention contemplates the use of Group I mGluR antagonists, preferably selective mGluR5 antagonists.

Exemplary mGluR5 antagonists include, without limitation, 2-methyl-6-(phenylethynyl)-pyridine (MPEP), (E)-6-methyl-2-styryl-pyridine (SIB 1893), LY293558, 2-methyl-6-[(1E)-2-phenylethynyl]-pyridine, 6-methyl-2-(phenylazo)-3-pyridinol, (RS)-α-methyl-4-carboxyphenylglycine (MCPG), 3S,4aR,6S,8aRS-6-((((1H-tetrazole-5-yl)methyl)oxy)methyl)-1,2,3,4,4a,5,6,7,8,8a-decahydroisoquinoline-3-carboxylic acid, 3S,4aR,6S,8aR-6-((((1H-tetrazole-5-yl)methyl)oxy)methyl)-1,2,3,4,4a,5,6,7,8,8a-decahydroisoquinoline-3-carboxylic acid, 3SR,4aRS,6SR,8aRS-6-(((4-carboxy)phenyl)methyl)-1,2,3,4,4a,5,6,7,8,8a-decahydroisoquinoline-3-carboxylic acid and 3 S,4aR,6S,8aR-6-(((4-carboxy)-phenyl)methyl)-1,2,3,4,4a,5,6,7,8,8a-decahydroisoquinoline-3-carboxylic acid, and their pharmaceutically acceptable salts, analogues and derivatives thereof.

Antagonists of mGluR5 are also described in WO 01/66113, WO 01/32632, WO 01/14390, WO 01/08705, WO 01/05963, WO 01/02367, WO 01/02342, WO 01/02340, WO 00/20001, WO 00/73283, WO 00/69816, WO 00/63166, WO 00/26199, WO 00/26198, EP-A-0807621, WO 99/54280, WO 99/44639, WO 99/26927, WO 99/08678, WO 99/02497, WO 98/45270, WO 98/34907, WO 97/48399, WO 97/48400, WO 97/48409, WO 98/53812, WO 96/15100, WO 95/25110, WO 98/06724, WO 96/15099 WO 97/05109, WO 97/05137, U.S. Pat. Nos. 6,218,385, 5,672,592, 5,795,877, 5,863,536, 5,880,112, 5,902,817, allowed U.S. application Ser. Nos. 08/825,997, 08/833,628, 08/842,360, and 08/899,319, all of which are hereby incorporated by reference.

For example, different classes of mGluR5 antagonists are described in WO 01/08705 (pp. 3-7), WO 99/44639 (pp. 3-11), and WO 98/34907 (pp. 3-20).

Another class of mGluR1 antagonists, antisense oligonucleotides, is described in WO 01/05963. Antisense oligonucleotides to mGluR5 can be prepared by analogy and used to selectively antagonize mGluR5, as desired.

Another class of mGluR5 antagonists is described in WO 01/02367 and WO 98/45270. Such compounds generally have the formula:

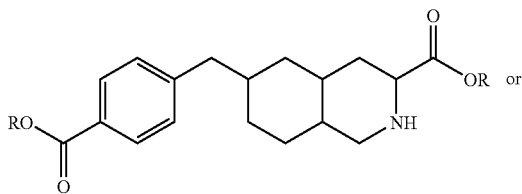

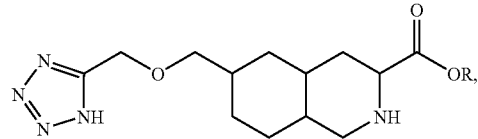

wherein R represents H or a hydrolyzable hydrocarbon moiety such as an alkyl, heteroalkyl, alkenyl, or aralkyl moiety.

In certain such embodiments, the isoquinoline system has the stereochemical array

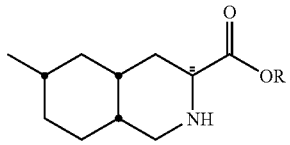

(wherein, as is known in the art, a dark spot on a carbon indicates hydrogen coming out of the page, and a pair of dashes indicates a hydrogen extending below the plane of the page), the enantiomer thereof, of a racemic mixture of the two.

Another class of antagonists, described in WO 01/66113, has the formula:

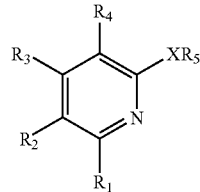

wherein $R_1$ denotes hydrogen, lower alkyl, hydroxyl-lower alkyl, lower alkyl-amino, piperidino, carboxy, esterified carboxy, amidated carboxy, unsubstituted or lower alkyl-, lower alkoxy-, halo- and/or trifluoromethyl-substituted N-lower-alkyl-N-phenylcarbamoyl, lower alkoxy, halo-lower alkyl or halo-lower alkoxy;

$R_2$ denotes hydrogen, lower alkyl, carboxy, esterified carboxy, amidated carboxy, hydroxyl-lower alkyl, hydroxyl, lower alkoxy or lower alkanoyloxy, 4-(4-fluoro-benzoyl-piperidin-1-ylcarboxy, 4-t.butyloxycarbonyl-piperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy;

$R_3$ represents hydrogen, lower alkyl, carboxy, lower alkoxy-carbonyl, lower alkyl-carbamoyl, hydroxy-lower alkyl, di-lower alkyl-aminomethyl, morpholinocarbonyl or 4-(4-fluoro-benzoyl)-piperadin-1-yl-carboxy;

$R_4$ represents hydrogen, lower alkyl, hydroxy, hydroxy-lower alkyl, amino-lower alkyl, lower alkylamino-lower alkyl, di-lower alkylamino-lower alkyl, unsubstituted or hydroxy-substituted lower alkyleneamino-lower alkyl, lower alkoxy, lower alkanoyloxy, amino-lower alkoxy, lower alkylamino-lower alkoxy, di-lower alkylaino-lower alkoxy, phthalimido-lower alkoxy, unsubstituted or hydroxy-or-2-oxo-imidazolidin-1-yl-substituted lower alkyleneamino-lower alkoxy, carboxy, esterified or amidated carboxy, carboxy-lower alkoxy or esterified carboxy-lower alkoxy; and X represents an optionally halo-substituted lower alkenylene or alkynylene group bonded via vicinal saturated carbon atoms or an azo (—N=N—) group, and $R_5$ denotes an aromatic or heteroaromatic group which is unsubstituted or substituted by one or more substituents selected from lower alkyl, halo, halo-lower alkyl, halo-lower alkoxy, lower alkenyl, lower alkynyl, unsubstituted or lower alkyl-, lower alkoxy-, halo- and/or trifluoromethyl-substituted phenyl, unsubstituted or lower alkyl-, lower alkoxy-, halo and/or trifluoromethyl-substituted phenyl-lower alkynyl, hydroxy, hydroxy-lower alkyl, lower alkanoyloxy-lower alkyl, lower alkoxy, lower alkenyloxy, lower alkylenedioxy, lower alkanoyloxy, amino-, lower alkylamino-, lower alkanoylamino- or N-lower alkyl-N-lower alkanoylamino-lower alkoxy, unsubstituted or lower alkyl-, lower alkoxy-, halo- and/or trifluoromethyl-substituted phenoxy, unsubstituted or lower alkyl-, lower alkoxy-, halo and/or trifluoromethyl-substituted phenyl-lower alkoxy, acyl, carboxy, esterified carboxy, amidated carboxy, cyano, carboxy-lower alkylamino, esterified carboxy-lower alkylamino, amidated carboxy-lower alkylamino, phosphono-lower alkylamino-esterified phosphono-lower alkylamino, nitro, amino, lower alkylamino, di-lower alkylamino-acylamino, N-acyl-N-lower alkylamino, phenylamino, phenyl-lower alkylamino, cycloalkyl-lower alkylamino or heteroaryl-lower alkylamino each of which may be unsubstituted or lower alkyl-, lower alkoxy-, halo- and/or trifluoromethyl-substituted; their N-oxides and their pharmaceutically acceptable salts.

In certain such embodiments, as disclosed in WO 01/66113 and WO 00/20001, these compounds have the formula:

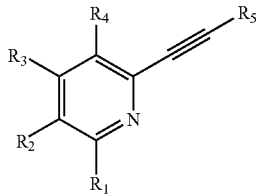

wherein $R_1$ is hydrogen, $(C_{1-4})$alkyl, $(C_{1-4})$alkoxy, cyano, ethynyl or di$(C_{1-4})$alkylamino, $R_2$ is hydrogen, hydroxy, carboxy, $(C_{1-4})$ alkoxycarbonyl, di$(C_{1-4})$alkylaminomethyl, 4-(4-fluoro-benzoyl)-piperidin-1-yl-carboxy, 4-t-butyloxycarbonyl-piperazin-1-yl-carboxy, 4-(4-azido-2-hydroxybenzoyl)-piperazin-1-yl-carboxy, or 4-(4-azido-2-hydroxy-3-iodo-benzoyl)-piperazin-1-yl-carboxy, $R_3$ is hydrogen, $(C_{1-4})$alkyl, carboxy, $(C_{1-4})$alkoxycarbonyl, $(C_{1-4})$alkylcarbamoyl, hydroxy$(C_{1-4})$alkyl, di$(C_{1-4})$alkylaminomethyl, morpholinocarbonyl or 4-(4-fluoro-benzoyl)-piperazin-1-yl-carboxy, $R_4$ is hydrogen, hydroxyl, carboxy, $C_{(2-5)}$alkanoyloxy, $(C_{1-4})$alkoxycarbonyl, amino $(C_{1-4})$alkoxy, di$(C_{1-4})$alkylamino$(C_{1-4})$alkoxy, di$(C_{1-4})$alkylamino$(C_{1-4})$alkyl or hydroxy$(C_{1-4})$alkyl, and $R_5$ is a group of formula:

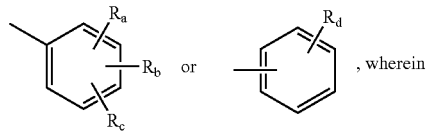

$R_a$ and $R_b$ independently are hydrogen, halogen, nitro, cyano, $(C_{1-4})$alkyl, $(C_{1-4})$alkoxy, trifluoromethyl, trifluoromethoxy or $(C_{2-5})$alkynyl, and $R_c$ is hydrogen, fluorine, chlorine bromine, hydroxy-$(C_{1-4})$alkyl, $(C_{2-5})$alkanoyloxy, $(C_{1-4})$alkoxy, or cyano, and $R_d$ is hydrogen, halogen or $(C_{1-4})$alkyl;

in free form or in the form of pharmaceutically acceptable salts.

In certain other embodiments disclosed in WO 01/66113, mGluR5 antagonists have structures of the formula:

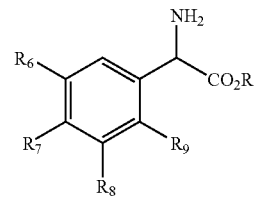

wherein $R_6$ is hydrogen, hydroxy, or $C_{1-6}$ alkoxy;

$R_7$ is hydrogen, carboxy, tetrazolyl, —SO$_2$H, —SO$_3$H, —OSO$_3$H, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl, or aryl $C_{1-6}$ aryl;

$R_8$ is hydrogen, hydroxy or $C_{1-4}$ alkoxy; and $R_9$ is fluoro, trifluoromethyl, nitro, $C_{1-6}$ alkyl, $C_{3-7}$ cycloalkyl, $C_{2-6}$ alkenyl, $C_{2-6}$ alkynyl, $C_{1-6}$ alkylthio, heteroaryl, optionally substituted aryl, optionally substituted aryl $C_{1-6}$ alkyl, optionally substituted aryl $C_{2-6}$ alkenyl, optionally substituted aryl $C_{2-6}$ alkynyl, optionally substituted aryloxy, optionally substituted $C_{1-6}$ alkoxy, optionally substituted arythio, optionally substituted aryl $C_{1-6}$ alkylthio, —CONR"R'", —NR"R'", —OCONR"R'" or —SONR"R'", where R" and R'" are each hydrogen, $C_{1-6}$ alkyl or aryl $C_{1-6}$ alkyl, or R" and R'" together form a $C_{3-7}$ alkylene ring;

or a salt or ester thereof.

Yet another class of mGluR5 antagonists is described in WO 00/63166. These compounds have the formula:

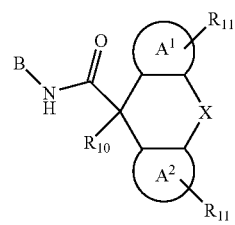

wherein $R_{10}$ signifies hydrogen or lower alkyl;

$R_{11}$ signifies, independently for each occurrence, hydrogen, lower alkyl, lower alkoxy, halogen or trifluoromethyl;

X signifies O, S, or two hydrogen atoms not forming a bridge;

$A^1/A^2$ signify, independently from each other, phenyl or a 6-membered heterocycle containing 1 or 2 nitrogen atoms;

B is a group of formula

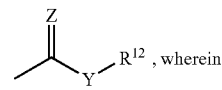

$R^{12}$ signifies lower alkyl lower alkenyl, lower alkynyl, benzyl, lower alkyl-cycloalkyl, lower alkyl-cyano, lower alkyl-pyridinyl, lower alkyl-lower alkoxy-phenyl, lower alkyl-phenyl (optionally substituted by lower alkoxy), phenyl (optionally substituted by lower alkoxy), lower alkyl-thienyl, cycloalkyl, lower alkyl-trifluoromethyl, or lower alkyl-morpholinyl;

Y signifies —O—, —S— or bond;
Z signifies —O— or —S—;
or B is a 5-membered heterocyclic group of formulas

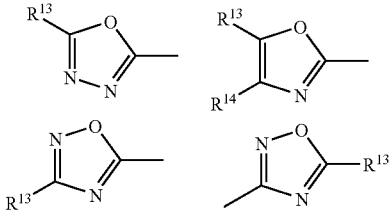

wherein
$R^{13}$ and $R^{14}$ independently signify hydrogen, lower alkyl, lower alkoxy, cyclohexyl, lower alkyl-cyclohexyl or trifluoromethyl, with the proviso that at least one of $R^{13}$ or $R^{14}$ is hydrogen;

as well as with their pharmaceutically acceptable salts.

Another class of mGluR1 antagonists is described in WO 01/32632. These compounds have the formula:

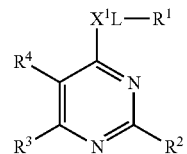

$X^1$ represents O or NH;
L represents a bond or a (1-6C) alkylene chain optionally interrupted by O, S, SO, SO or NH and optionally substituted on an alkylene carbon atom by fluoro, hydroxy, (1-4C)alkoxy or oxo;
$R^1$ represents an unsubstituted or substituted carbocyclic or heterocyclic group;
$R^2$ represents a hydrogen atom, a halogen atom, a carboxyl group, a cyano group, a $SCH_2CN$, or a group of formula $X^2$-$R^5$ in which $X^2$ represents a bond, O, S, SO, $SO_2$ or NH and $R^5$ represents (1-8C)alkyl, (3-10C)cycloalkyl, halo(1-6C)alkyl, hydroxy(1-6C)alkyl, dihydroxy(1-4C)alkyl, (1-4C)alkoxy(1-4C)alkyl, (1-4C)alkanoyl(1-4C)alkyl, (1-4C)alkanoyloxy(1-4C)alkyl, carboxy(1-4C)alkyl, (1-4C)alkylaminocarbonyl(1-4C)alkyl, (1-4C)alkanoylamino, (1-4C)alkanoylamino(1-4C)alkyl, (1-4C)alkanoylamino[(1-4C)alkyl]$_2$, (1-4C)alkylthio(1-4C)alkyl, (1-4C) alkylsulfinyl(1-4C)alkyl, (1-4C)alkylsulfonyl(1-4C)alkyl, (1-4C)alkylsulfonylamino)(1-4C)alkyl, (1-4C)alkylamino-sulfonyl)(1-4C)alkyl, di(1-4C)alkylaminophosphonyl)(1-4C)alkyl, phenyl or phenyl(1-4C)alkyl in which any phenyl group is unsubstituted or substituted by one or two substituents selected independently from a halogen atom, (1-4C)alkyl and (1-4C)alkoxy; and
$R^3$ and $R^4$ each independently represents (1-4C)alkyl or together with the carbon atoms to which they are attached form an unsubstituted or substituted carbocyclic or heterocyclic ring;

or a pharmaceutically acceptable salt thereof.

Another class of mGluR5 antagonists is described in WO 01/14390. These compounds have the formula:

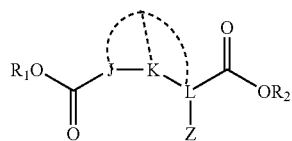

wherein,
either J and K are taken together with one or more additional atoms independently selected from the group consisting of C, O, S, and N in chemically reasonable substitution patterns to form a 3-7 membered saturated or unsaturated heterocyclic or carbocyclic ring, and L is —CH,
or J, K, and L are taken together with one or more additional atoms independently selected from the group consisting of C, O, S, and N in chemically reasonable substitution patterns to form a 4-8 membered saturated or unsaturated, mono-, bi-, or tricyclic, hetero- or carbocyclic ring structure;
Z is a metal chelating group;
$R_1$ and $R_2$ are independently hydrogen, $C_1$-$C_9$ alkyl, $C_2$-$C_9$ alkenyl, $C_3$-$C_8$ cycloalkyl, $C_5$-$C_7$ cycloalkenyl, or Ar, wherein each said alkyl, alkenyl, cycloalkyl, cycloalkenyl, or Ar is independently unsubstituted or substituted with one or more substituent(s); and
Ar is a carbocyclic or heterocyclic moiety which is unsubstituted or substituted with one or more substituent(s);

or a pharmaceutically acceptable equivalent thereof.

Still another class of mGluR5 antagonists is described in U.S. Pat. No. 6,218,385. These compounds have the formula:

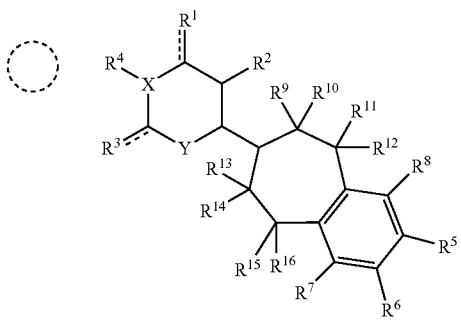

$R^1$ signifies hydrogen, hydroxy, lower alkyl, oxygen, halogen, or
—OR, —O($C_3$-$C_6$)cycloalkyl, —O(CHR)$_n$—($C_3$-$C_6$)cycloalkyl, —O(CHR)$_n$CN, —O(CHR)$_n$CF$_3$, —O(CHR)(CHR)$_n$NR$_2$, —O(CHR)(CHR)$_n$OR, —O(CHR)$_n$-lower alkenyl, —OCF$_3$, —OCF$_2$—R, —OCF$_2$-lower alkenyl, —OCHRF, —OCHF-lower alkenyl, —OCF$_2$CRF$_2$, —OCF$_2$ Br, —O(CHR)$_n$CF$_2$Br, —O(CHR)$_n$-phenyl, wherein the phenyl group may be optionally substituted independently from each other by one to three lower alkyl, lower alkoxy, halogen, nitro or cyano groups,
—O(CHR)(CHR)$_n$-morpholino, —O(CHR)(CHR)$_n$-pyrrolidino, —O(CHR)(CHR)$_n$-piperidino, —O(CHR)(CHR)$_n$-imidazolo, —O(CHR)(CHR)$_n$-triazolo, —O(CHR)$_n$-pyridino, —O(CHR)(CHR)$_n$—OSi-lower alkyl, —O(CHR)(CHR)$_n$OS(O)$_2$-lower alkyl, —(CH$_2$)$_n$CH=CF$_2$, —O(CHR)$_n$-2,2-dimethyl-[1,3]dioxolane, —O(CHR)$_n$—CHOR—CH$_2$OR, —O(CHR)$_n$—CHOR—(CHR)$_n$—CH$_2$OR or
—SR or —S(CHR)$_n$COOR, or
—NR$_2$, —N(R)(CHR)(CHR)$_n$OR, —N(R)(CHR)$_n$CF$_3$, —N(R)(CHR)(CHR)$_n$-morpholino, —N(R)(CHR)(CHR)$_n$-imidazolo, —N(R)(CHR)(CHR)$_n$-pyrrolidino, —N(R)(CHR)(CHR)$_n$-pyrrolidin-2-one, —N(R)(CHR)(CHR)$_n$-piperidino, —N(R)(CHR)(CHR)$_n$-triazolo, —N(R)(CHR)$_n$-pyridino, or
$R^1$ and $R^4$ are interconnected to the groups —(CH$_2$)$_{3-5}$—, —(CH$_2$)$_2$—N=, —CH=N—N=—, —CH=CH—N=, —NH—CH=CH— or —NR—CH$_2$—CH$_2$— and form together with any N or C atoms to which they are attached an additional ring;

n is 1-6;

R signifies hydrogen, lower alkyl or lower alkenyl, independently from each other, if more than one R is present;

R$^2$ signifies nitro or cyano;

R$^3$ signifies hydrogen, lower alkyl, =O, —S, —SR, —S(O)$_2$-lower alkyl,
—(C$_3$-C$_6$)cycloalky or piperazino, optionally substituted by lower alkyl, or
—CONR$_2$, —(CHR)$_n$CONR$_2$, —(CHR)$_n$OR, —(CH$_2$)$_n$—CF$_3$, —CF$_3$, —(CHR)$_n$OC(O)CF$_3$, —(CHR)$_n$COOR, —(CHR)$_n$SC$_6$H$_5$, wherein the phenyl group may be optionally substituted independently from each other by one to three lower alkyl, lower alkoxy, halogen, nitro or cyano groups,
—(CHR)$_n$-1,3-dioxo-1,3-dihydro-isoindol, —(CHR)$_n$-tetrahydro-pyran-2-yloxy or —(CHR)$_n$—S-lower alkyl, or
—NR$_2$, —NRCO-lower alkyl, —NRCHO, —N(R)(CHR)$_n$CN, —N(R)(CHR)$_n$CF$_3$, —N(R)(CHR)(CHR)$_n$—OR, —N(R)C(O)(CHR)$_n$O-lower alkyl,
—NR(CHR)$_n$-lower alkyl, —NR(CHR)(CHR)$_n$—OR,
—N(R)(CHR)(CHR)$_n$—O-phenyl, wherein the phenyl group may be optionally substituted independently from each other by one to three lower alkyl, lower alkoxy, halogen, nitro or cyano groups,
—N(R)(CHR)$_n$-lower alkenyl, —N(R)(CHR)(CHR)$_n$—O—(CHR)$_n$OR, —N(R)(CHR)$_n$C(O)O-lower alkyl, —N(R)(CHR)$_n$C(O)NR-lower alkyl, —N(R)(CH$_2$)$_n$-2,2-dimethyl-[1,3]dioxolane, —N(R)(CHR)(CHR)$_n$ morpholino, —N(R)(CHR)$_n$-pyridino, —N(R)(CHR)(CHR)$_n$-piperidino, —N(R)(CHR)(CHR)$_n$-pyrrolidino, —N(R)(CHR)(CHR)$_n$—O-pyridino, —N(R)(CHR)(CHR)$_n$ imidazolo, —N(R)(CHR)$_n$—CR$_2$—(CHR)$_n$—OR, —N(R)(CHR)$_n$—CR$_2$—OR, —N(R)(CHR)$_n$—CHOR—CH$_2$OR, —N(R)(CHR)$_n$—CHOR—(CHR)$_n$—CH$_2$OR, or
—OR, —O(CHR)$_n$CF$_3$, —OCF$_3$, —O(CHR)(CHR)$_n$—O-phenyl, wherein the phenyl group maybe optionally substituted independently from each other by one to three lower alkyl, lower alkoxy, halogen, nitro or cyano groups,
O(CHR)(CHR)$_n$—O-lower alkyl, —O(CHR)$_n$-pyridino or —O(CHR)(CHR)$_n$-morpholino;

or R$^3$ and R$^4$ are interconnected to the groups —(CH$_2$)$_{3-5}$—, —(CH$_2$)$_2$—N=, —CH=N—N=—, —CH=CH—N=, —NH—CH=CH— or NR—CH$_2$—CH$_2$— and form together with any N or C atoms to which they are attached an additional ring; and R$^4$ signifies hydrogen, lower alkyl, lower alkenyl or nitro, or
—OR, —OCF$_3$, —OCF$_2$—R, —OCF$_2$-lower alkenyl, —OCHRF, —OCHF-lower alkenyl, —O(CHR)$_n$CF$_3$, or
—(CHR)$_n$CHRF, —(CHR)$_n$CF$_2$R, —(CHR)$_n$CF$_3$, —(C$_3$-C$_6$)cycloalkyl, —(CHR)$_n$(C$_3$-C$_6$)cycloalkyl, —(CHR)$_n$CN, —(CHR)$_n$-phenyl, wherein the phenyl group may be optionally substituted independently from each other by one, to three lower alkyl, lower alkoxy, halogen, nitro or cyano groups,
—(CHR)(CHR)$_n$OR, —(CHR)$_n$CHORCH$_2$OR; —(CHR)(CHR)$_n$NR$_2$, —(CHR)$_n$COOR, —(CHR)(CHR)$_n$OSi-lower alkyl, —(CHR)(CHR)$_n$—OS(O)$_2$-lower alkyl, —(CH$_2$)$_n$—CH=CF$_2$, —CF$_3$, —CF$_2$—R, —CF$_2$-lower alkenyl, —CHRF, —CHF-lower alkenyl, —(CHR)$_n$-2,2-dimethyl-[1,3]dioxolane, —(CH$_2$)$_n$-2-oxo-azepan-1-yl, —(CHR)(CHR)$_n$-morpholino, —(CHR)$_n$-pyridino, —(CHR)(CHR)$_n$-imidazolo, —(CHR)(CHR)$_n$-triazolo, —(CHR)(CHR)$_n$-pyrrolidino, optionally substituted by —(CH$_2$)$_n$OH, —(CHR)(CHR)$_n$-3-hydroxy-pyrrolidino or —(CHR)(CHR)$_n$-piperidino, or
NR$_2$, —N(R)(CHR)$_n$-pyridino, —N(R)C(O)O-lower alkyl, —N(CH$_2$CF$_3$)C(O)O-lower alkyl, —N[C(O)O-lower alkyl]$_2$, —NR—NR—C(O)O-lower alkyl or —N(R)(CHR)$_n$CF$_3$, —NRCF$_3$, —NRCF$_2$—R, —NRCF$_2$-lower alkenyl, —NRCHRF, —NRCHP-lower alkenyl;
or is absent if X is —N= or =N—;

R$^5$, R$^6$ signify hydrogen, lower alkyl, lower alkoxy, amino, nitro, —SO$_2$NH$_2$ or halogen; or R$^5$ and R$^6$ are interconnected to the group —O—CH$_2$—O— and form together with the C atoms to which they are attached an additional 5-membered ring;

R$^7$, R$^8$ signify hydrogen, lower alkyl, lower alkoxy, amino, nitro or halogen;

R$^9$, R$^{10}$ signify hydrogen or lower alkyl;

R$^{11}$, R$^{12}$ signifies hydrogen, lower alkyl, hydroxy, lower alkoxy, lower alkoxycarbonyloxy or lower alkanoyloxy;

R$^{13}$, R$^{14}$ signify hydrogen, tritium or lower alkyl;

R$^{15}$, R$^{16}$ signifies hydrogen, tritium, lower alkyl, hydroxy, lower alkoxy or are together an oxo group; or X signifies —N=, =N—, —N<, >C= or =C<;

Y signifies —N=, =N—, —NH—, —CH= or =CH—; and the dotted line may be a bond when R$^1$, R$^3$ or R$^4$ represent a bivalent atom, as well as with the pharmaceutically acceptable salts of each compound of the above formula and the racemic and optically active forms of each compound of the above formula.

Yet other classes of mGluR5 antagonists are described in WO 01/02342 and WO 01/02340. These compounds have the formulas, respectively:

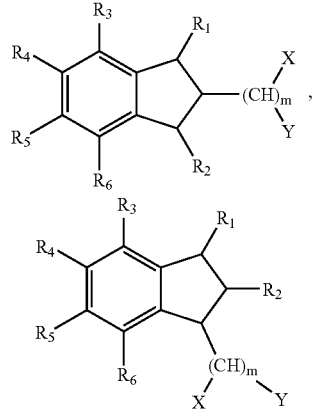

stereoisomers thereof, or pharmaceutically acceptable salts or hydrates thereof, wherein:

R1, and R2 are selected from the group comprising:
1) H; or
2) an acidic group selected from the group comprising carboxy, phosphono, phosphino, sulfono, sulfino, borono, tetrazol, isoxazol, —(CH$_2$)$_n$-carboxy, —(CH$_2$)$_n$-phosphono, —(CH$_2$)$_n$-phosphino, —(CH$_2$)$_n$-sulfono, —(CH$_2$)$_n$-sulfino, —(CH$_2$)$_n$-borono, —(CH$_2$)$_n$-tetrazol, and —(CH$_2$)$_n$-isoxazol, where n=1, 2, 3, 4, 5, or 6; or X is an acidic group selected from the group comprising carboxy, phosphono, phosphino, sulfono, sulfino, borono, tetrazol, isoxazol;

Y is a basic group selected from the group comprising 1° amino, 2° amino, 3° amino, quaternary ammonium salts, aliphatic 1° amino, aliphatic 2° amino, aliphatic 3° amino, aliphatic quaternary ammonium salts, aromatic 1° amino, aromatic 2° amino, aromatic 3° amino, aromatic quaternary ammonium salts, imidazol, guanidino, boronoamino, allyl, urea, thiourea;

m is 0, 1;

R3, R4, R5, R6 are independently H, nitro, amino, halogen, tritium, trifluoromethyl, trifluoroacetyl, sulfo, carboxy, carbamoyl, sulfamoyl or acceptable esters thereof;

or a salt thereof with a pharmaceutically acceptable acid or base.

Further classes of mGluR5 antagonists are described in WO 00/73283 and WO 99/26927. These compounds have the formula: R—[Linker]—Ar;

wherein R is an optionally substituted straight or branched chain alkyl, arylalkyl, cycloalkyl, or alkylcycloalkyl group preferably containing 5-12 carbon atoms. Ar is an optionally substituted aromatic, heteroaromatic, arylalkyl, or heteroaralkyl moiety containing up to 10 carbon atoms and up to 4 heteroatoms, and [linker] is —(CH$_2$)$_n$—, where n is 2-6, and wherein up to 4 CH$_2$ groups may independently be substituted with groups selected from the group consisting of C$_1$-C$_3$ alkyl, CHOH, CO, O, S, SO, SO$_2$, N, NH, and NO. Two heteroatoms in the [linker] may not be adjacent except when those atoms are both N (as in —N═N— of —NH—NH—) or are N and S as in a sulfonamide. Two adjacent CH$_2$ groups in [linker] also may be replaced by a substituted or unsubstituted alkene or alkyne group. Pharmaceutically acceptable salts of the compounds also are provided.

Another class of mGluR5 antagonists is described in WO 00/69816. These compounds have the formula:

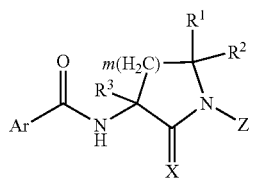

wherein, n is 0, 1 or 2;

X is O, S, NH, or NOH;

R$^1$ and R$^2$ are each independently H, CN, COOR, CONHR, C$_1$-C$_6$ alkyl, tetrazole, or R$^1$ and R$^2$ together represent "═O";

R is H or C$_1$-C$_6$ alkyl;

R$^3$ is C$_1$-C$_6$ alkyl, C$_2$-C$_6$ alkenyl, C$_3$-C$_6$ cycloalkyl, —CH$_2$OH, —CH$_2$O-alkyl, —COOH;

Ar is an unsubstituted or substituted aromatic or heteroaromatic group;

Z represents a group of the formulae

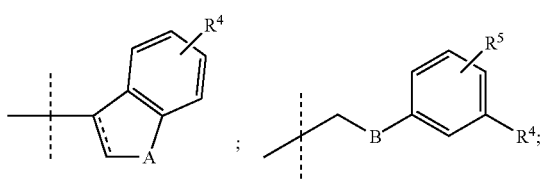

-continued

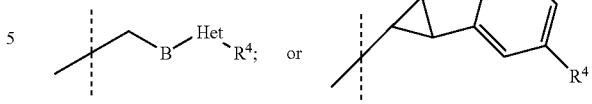

wherein,

R$^4$ and R$^5$ are each independently H, halogen, C$_1$-C$_6$ alkoxy, —OAr, C$_1$-C$_6$ alkyl, —CF$_3$, COOR, CONHR, —CN, —OH, —COR, —S—(C$_1$-C$_6$ alkyl), —SO$_2$(C$_1$-C$_6$ alkyl);

A is CH$_2$, O, NH, NR, S, SO, SO$_2$, CH$_2$—CH$_2$, CH$_2$O, CHOH, C(O); wherein R is as defined above;

B is CHR, CR$_2$, C$_1$-C$_6$ alkyl, C(O), —CHOH, —CH$_2$—O, —CH═CH, CH$_2$—C(O), CH$_2$—S, CH$_2$—S(O), CH$_2$—SO$_2$; —CHCO$_2$R; or —CH—NR$_2$, wherein R is as defined above;

Het is a heterocycle such as furan, thiophene, or pyridine;

or a pharmaceutically acceptable salt thereof.

Yet other classes of mGluR1 antagonists are described in WO 00/26199 and WO 00/26198. These compounds have the formula:

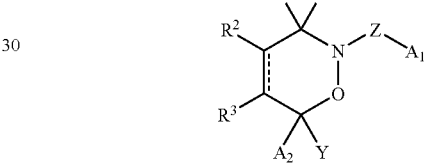

in which,

R$^1$, R$^2$ and R$^3$ are independently hydrogen, (C$_1$-C$_6$)alkyl, (C$_2$-C$_6$)alkenyl, (C$_3$-C$_{10}$)cycloalkyl, unsubstituted or substituted aryl, unsubstituted or substituted aryl(C$_1$-C$_6$)alkyl, unsubstituted or substituted aryl(C$_2$-C$_6$)alkenyl, halo, carboxy, (C$_1$-C$_6$)alkoxycarbonyl or —(CH$_2$)$_m$—OH, wherein m is 1, 2 or 3;

═ indicates a single or a double bond;

X and Y are each independently hydrogen, or X and Y together represent a bridge of the formula —(CH$_2$)$_n$—, where n is 1 or 2;

A$_1$ and A$_2$ are each independently an unsubstituted or substituted aryl;

Z is —CO—, —SO$_2$— or —CH2—; provided that, when Z is —CO—, A$_1$ is not 3,4,5-trimethoxyphenyl;

or a pharmaceutically acceptable salt or ester thereof.

Another class of mGluR5 antagonists is described in WO 99/54280. These compounds have the formula:

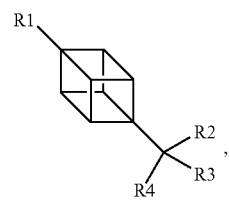

wherein,

R1 can be an acidic group selected from the group consisting of carboxyl, phosphono, phosphino, sulfono, sulfino, borono, tetrazol, isoxazol, —CH$_2$-carboxyl, —CH$_2$-phosphono, —CH$_2$-phosphino, —CH$_2$-sulfono, —CH$_2$-sulfino, —CH$_2$-borono, —CH$_2$-tetrazol, —CH$_2$-isoxazol and higher homologues thereof;

R2 can be a basic group selected from the group consisting of 1° amino, 2° amino, 3° amino, quaternary ammonium salts, aliphatic 1° amino, aliphatic 2° amino, aliphatic 3° amino, aliphatic quaternary ammonium salts, aromatic 1° amino, aromatic 2° amino, aromatic 3° amino, aromatic quaternary ammonium salts, imidazol, guanidino, boronoamino, allyl, urea, thiourea;

R3 can be H, aliphatic, aromatic or heterocyclic;

R4 can be an acidic group selected from the group consisting of carboxyl, phosphono, phosphino, sulfono, sulfino, borono, tetrazol, isoxazol;

stereoisomers thereof;

and pharmaceutically acceptable salts thereof.

Yet another class of mGluR5 antagonists is described in WO 99/08678. These compounds have the formula:

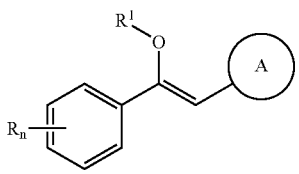

wherein R signifies halogen or lower alkyl;

n signifies 0-3;

R$^1$ signifies lower alkyl; cycloalkyl; benzyl optionally substituted by hydroxy, halogen, lower alkoxy or lower alkyl; benzoyl optionally substituted by amino, lower alkylamino or di-lower alkylamino; acetyl or cycloalkyl-carbonyl; and

signifies an aromatic 5-membered residue which is bonded via a N-atom and which contains further 1-3 N atoms in addition to the linking N atom, as well as their pharmaceutically acceptable salts.

Preferred antagonists are those that provide a reduction of activation by the ligand of at least 10%, and more preferably at least 20%, at least 30%, at least 40%, at least 50%, at least 60%, at least 70%, at least 80%, at least 90%, at least 95%, or even at least 99% at a concentration of the antagonist, for example, of 1 µg/ml, 10 µg/ml, 100 µg/ml, 500 µg/ml, 1 mg/ml, 10 mg/ml, or 100 mg/ml. The percentage antagonism represents the percentage decrease in activity of mGluR, e.g., mGluR5, in a comparison of assays in the presence and absence of the antagonist. Any combination of the above mentioned degrees of percentage antagonism and concentration of antagonist may be used to define an antagonist of the invention, with greater antagonism at lower concentrations being preferred.

An antagonist for use in the invention may be a relatively non-specific antagonist that is an antagonist of mGluRs in general. Preferably, however, an antagonist selectively antagonizes group I mGluRs. Even more preferably, an antagonist used in the invention is a selective antagonist of mGluR5. A selective antagonist of mGluR5 is one that antagonizes mGluR5, but antagonizes other mGluRs only weakly or substantially not at all, or at least antagonizes other mGluRs with an EC$_{50}$ at least 10 or even 100 or 1000 times greater than the EC$_{50}$ at which it antagonizes mGluR5. Most preferred antagonists are those which can selectively antagonize mGluR5 at low concentrations, for example, those that cause a level of antagonism of 50% or greater at a concentration of 100 µg/ml or less.

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of potential mGluR antagonists, can be screened rapidly in high-throughput assays to identify potential lead compounds, as well as to refine the specificity, toxicity, and/or cytotoxic-kinetic profile of a lead compound.

Simply for illustration, a combinatorial library for the purposes of the present invention is a mixture of compounds, such as chemically related compounds, which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject antagonists. See, for example, Blondelle et al. (1995) Trends Anal. Chem. 14:83; the Affymax U.S. Pat. Nos. 5,359,115 and 5,362,899: the Ellman U.S. Pat. No. 5,288, 514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject antagonists can be synthesized and screened for a particular activity or property.

In an exemplary embodiment, a library of candidate antagonist diversomers can be synthesized utilizing a scheme adapted to the techniques described in the Still et al. PCT publication WO 94/08051, e.g., being linked to a polymer bead by a hydrolyzable or photolyzable group e.g., located at one of the positions of the candidate antagonists or a substituent of a synthetic intermediate. According to the Still et al. technique, the library is synthesized on a set of beads, each bead including a set of tags identifying the particular diversomer on that bead. The diversomers can be released from the bead, e.g., by hydrolysis and tested for activity.

A) Direct Characterization

A growing trend in the field of combinatorial chemistry is to exploit the sensitivity of techniques such as mass spectrometry (MS), for example, which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (991) *Tetrahedron Lett* 32:6163-6166).

C) Divide-Couple-Recombine

In yet another embodiment, a variegated library of compounds can be provided on a set of beads utilizing the strategy of divide-couple-recombine (see, for example, Houghten (1985) *PNAS* 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially addressable synthesis. In one embodiment, the combinatorial process is carried out by controlling the addition of a chemical reagent to specific locations on a solid support (Dower et al. (1991) *Annu Rep Med Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) *PNAS* 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr et al. (1993) *JACS* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

B. Exemplary mGLuR5 Antagonist Assays

Methods for identifying mGluR antagonists which may be used in a method of treatment of the human or animal body by therapy, in particular in the treatment of Down's Syndrome, Fragile X and other forms of mental retardation, schizophrenia and autism, are known in the art. Such methods essentially comprise determining whether a test agent is an mGluR5 antagonist and determining whether an antagonist so identified can be used in the treatment of Down's Syndrome, Fragile X, and/or autism.

One example of an assay for determining the activity of a test compound as an antagonist of mGluR5 comprises expressing mGluR5 in CHO cells which have been transformed with cDNAs encoding the mGluR5 receptor protein (Daggett et al., 1995, Neuropharmacology, 34, 871). The mGluR5 is then activated by the addition of quisqualate and/or glutamate and can be assessed by, for example the measurement of: (1) phosphoinositol hydrolysis (Litschig et al., 1999, Mol. Pharmacol. 55, 453); (ii) accumulation of [3H] cytidinephosphate-diacylglycerol (Cavanni et al., 1999, Neuropharmacology 38, A10); or fluorescent detection of calcium influx into cells Kawabata et al., 1996, Nature 383, 89-1; Nakahara et al., 1997, J. Neurochemistry 69, 1467). The assay may be carried out both in the presence and absence of a test product in order to determine whether the test compound can antagonize the activity of the test product. This assay is amenable to high throughput screening.

GluR5 receptor antagonists may also be identified by radiolabelled ligand binding studies at the cloned and expressed human GluR5 receptor (Korczak et al., 1994, Recept. Channels 3; 41-49), by whole cell voltage clamp electro-physiological recordings of functional activity at the human GluR5 receptor (Korczak et al., 1994, Recept. Channels 3; 41-49) and by whole cell voltage clamp electro-physiological recordings of currents in acutely isolated rat dorsal root ganglion neurons (Bleakman et al., 1996, Mol. Pharmacol. 49; 581-585).

Suitable control experiments can be carried out. For example, a putative antagonist of mGluR5 could be tested with mGluR1 in order to determine the specificity of the putative antagonist, or other receptors unrelated to mGluRs to discount the possibility that it is a general antagonist of cell membrane receptors.

Suitable test products for identifying an mGluR5 antagonist include combinatorial libraries, defined chemical identities, peptides and peptide mimetics, oligonucleotides and natural product libraries. The test products may be used in an initial screen of, for example, ten products per reaction, and the products of batches that show antagonism tested individually. Furthermore, antibody products (for example, monoclonal and polyclonal antibodies, single chain antibodies, chimeric bodies and CDR-grafted antibodies) may be used.

C. Pharmaceutical Preparations of the mGLuR5 Antagonists

In another aspect, the present invention provides pharmaceutical preparations comprising the subject mGluR5 antagonists. The mGluR5 antagonists for use in the subject method may be conveniently formulated for administration with a biologically acceptable, non-pyrogenic, and/or sterile medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the mGluR5 antagonists, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations."

Pharmaceutical formulations of the present invention can also include veterinary compositions, e.g., pharmaceutical preparations of the mGluR5 antagonist suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, can be used to form an implant for the sustained release of an mGluR5 antagonist at a particular target site.

The preparations of the present invention may be given orally, parenterally, topically, or rectally. They are, of course, given by forms suitable for the desired administration route. For example, they may be administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular reuptake inhibitors employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

While it is possible for a compound of the present invention to be administered alone, it is preferable to administer the compound as a pharmaceutical formulation (composition). The pharmaceutical composition according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, and pastes for application to the tongue; (2) parenteral administration, for example, by subcutaneous, intramuscular, or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "pharmaceutically acceptable carrier" as used herein means a pharmaceutically acceptable material, composition or vehicle, such as a liquid or solid filter, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present mGluR5 antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active reuptake inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the reuptake inhibitors in the proper medium. Absorption enhancers can also be used to increase the flux of the reuptake inhibitors across the skin. The rate of such flux can be controlled by either providing a rate-controlling membrane or dispersing the compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and Co., San Francisco, U.S.A., 1969 or "Livestock Feeds and Feeding" 0 and B books, Corvallis, Ore., U.S.A., 1977).

V. Exemplary Uses of the Compounds of the Invention

In one embodiment, the invention is directed to the use of an antagonist of a Group I mGluR, such as mGluR5, preferably of human mGluR5, in the manufacture of a medicament for use in a method of treating and preventing a mental condition such as Down's Syndrome, Fragile X, and other forms of mental retardation, schizophrenia or autism. In various embodiments, the present invention contemplates modes of treatment and prophylaxis which utilize one or more of the subject mGluR antagonists.

In another embodiment, the invention is an antagonist of a Group I mGluR, such as mGluR5, for use in a method of treatment of the human or animal body by therapy; a method of treating a host suffering from Fragile X, Down's Syndrome, and other forms of mental retardation, schizophrenia or autism, which method comprises administering to the host a therapeutically effective amount of an antagonist of mGluR5; a pharmaceutical composition comprising an antagonist of a Group I mGluR, such as mGluR5, and a pharmaceutically acceptable carrier or diluent; or a product containing an antagonist of a Group I mGluR, such as mGluR5, and a therapeutic substance as a combined preparation.

The neural mechanisms which underlie mental retardation are largely unknown. The discovery of the genetic basis of some forms of mental retardation, such as Fragile X syndrome, has provided insight into the cellular mechanisms responsible for the cognitive deficits associated with mental retardation. Fragile X syndrome is the most common inherited form of mental retardation, affecting 1 in 1500 men and 1 in 2500 women (de Vries, et al., 1993). Many patients with Fragile X syndrome exhibit many neurological deficiencies or conditions, including moderate to severe mental retardation (IQ=30-70), seizures (e.g., benign childhood epilepsy, temporal lobe epilepsy), visual spatial defects, anxiety, learning difficulties and certain characteristics of autism.

An embodiment of the invention is a method of treating a human with Fragile X syndrome, autism, Down's Syndrome, a neurological disorder or mental retardation to diminish, halt, ameliorate or prevent one or more of the above-mentioned deficiencies (e.g., anxiety, benign childhood epilepsy). In another embodiment, the invention is a method of treating a human without Fragile X syndrome who suffers from one or more of the above-mentioned deficiencies or conditions (e.g., anxiety, epilepsy).

In a particular embodiment, children with mental retardation, autism, Down's Syndrome and Fragile X syndrome can be treated with Group I mGluR antagonists. The children can be treated during infancy (between about 0 to about 1 year of life), childhood (the period of life between infancy and puberty) and during puberty (between about 8 years of life to about 18 years of life). In still another embodiment, the methods of the invention can be used to treat adults (greater than about 18 years of life) having mental retardation, Fragile X syndrome, schizophrenia, autism and Down's Syndrome. In a further embodiment of the invention, anxiety and epilepsy in children and adults having Fragile X syndrome, autism, mental retardation, Down's Syndrome and schizophrenia can be treated by administering to the children or the adult a Group I mGluR antagonist. In a particular embodiment, the Group I mGluR antagonist is an antagonist of mGluR5.

Unlike other forms of mental retardation, Fragile X patients exhibit no gross neuroanatomical deformities thought to give rise to cognitive deficits (Hinton, et al., 1991; Wisniewski, et al., 1991). Instead, there is a neuropathology on a smaller scale, at the level of the synapse. Cortical neurons of patients with Fragile X syndrome are characterized by reduced dendritic length and a number of irregular, very long, thin and tortuous dendritic spines, and a reduction in mature, short and stubby spines. These long, thin spines resemble immature spines or dendritic filopodia prevalent in developing neurons during synapse maturation (Fiala, et al., 1998). Similar dendritic pathologies are associated with other forms of mental retardation such as Down's or Rett syndrome (Marin-Padilla, 1972; Kaufmann and Moser, 2000). Therefore, malfunctions of dendritic development and function may be a common mechanism that underlies mental retardation.

The molecular basis for Fragile X syndrome was discovered when it was found that Fragile X patients have an expansion in the 5' untranslated region of the Fragile X mental retardation (FMR1) gene, which results in transcriptional silencing (reviewed by (Imbert, et al., 1998)). Therefore, the loss of the FMR1 gene product, Fragile X mental retardation protein (FMRP), is responsible for the Fragile X phenotype (Pieretti, et al., 1991; Verheij, et al., 1993). In support of this hypothesis, a mouse model of Fragile X syndrome was developed by a 'knockout' (KO) of the FMR1 gene (Bakker and Consortium, 1994). The FMR1-KO mice have many of the symptoms of the human Fragile X syndrome including learning deficits and hyperactivity (Fisch, et al., 1999; Paradee, et al., 1999).

Studies of the normal function of FMRP have indicated that FMRP is a regulator of protein synthesis or mRNA translation. FMRP has 2 RNA binding regions and associates with translating polyribosomes and a subset of brain mRNAs.

(Khandjian et al., 1996; Tamanini et al., 1996). A very rare but severe form of Fragile X syndrome is caused by a single amino acid mutation (1304N) in one of the RNA binding domains of FMRP. The severity of the Fragile X phenotype observed with the 1304N mutation indicates that RNA binding and association with polyribosomes is crucial to the function of FMRP (Siomi, et al., 1994). Interestingly, it is now known that polyribosomes and FMRP are present in dendritic spines and synapses have the ability to synthesize protein suggesting that FMRP may function specifically to regulate protein synthesis locally at synapses (Steward and Reeves, 1988; Feng, et al., 1997).

In recent years, a number of studies have demonstrated that mechanisms of activity-dependent synaptic strengthening or weakening, such as long-term potentiation (LTP) or long-term depression (LTD) respectively, contribute to synapse formation and maturation (reviewed by (Collin, et al., 1997; Constantine-Paton and Cline, 1998). Both LTP and LTD can reflect a change in the level of surface density of neurotransmitter receptors in the synaptic region of neuron membranes. For example the surface expression of either or both of the NMDA receptor or the AMPA receptor may be reduced in LTD or increased in LTP. Therefore, an alteration in activity-dependent synaptic plasticity during synapse maturation may be one underlying source of the spine abnormalities and Fragile X phenotype. Furthermore, persistent modifications at the level of the synapse are thought to be the neural basis of learning and memory in the adult. Altered activity-dependent plasticity in mature brains of affected patients may be a factor in the learning deficiencies experienced in Fragile X syndrome.

Autism is a disabling neurological disorder that affects thousands of Americans and encompasses a number of subtypes, with various putative causes and few documented ameliorative treatments. The disorders of the autistic spectrum may be present at birth, or may have later onset, for example, at age two or three. There are no clear-cut biological markers for autism. Diagnosis of the disorder is made by considering the degree to which the child matches the behavioral syndrome, which is characterized by deficits in sociability, reciprocal verbal and nonverbal communication along with restricted, repetitive or stereotypical behavior.

A genetic basis for autism is suggested by observations such as developmental anomalies in autistic patients, increased incidence of autism in siblings of autistic patients, and a tendency for both of a set of monozygotic twins to be either autistic or not autistic (also called "concordance" for a disorder). However, in most (75-80%) autistic individuals, no underlying cause is found for the autism. Previous studies have implicated abnormalities involving neurotransmitters including serotonin, norepinephrine, and histamine in some cases of autism. Other causative factors may include rubella, problems during pregnancy, labor and delivery, cytomegalic inclusion disease, phenylketonuria, and Fragile X syndrome. Autistic children are also at increased risk of developing seizure disorders, e.g., epilepsy, especially during their teen years.

A number of different treatments for autism have been developed. Many of the treatments, however, address the symptoms of the disease rather than the causes. For example, therapies ranging from psychoanalysis to psychopharmacology have been employed in the treatment of autism. Although some clinical symptoms may be lessened by these treatments, modest improvement, at best, has been demonstrated in only a minor fraction of the cases. Only a small percentage of autistic persons become able to function as self-sufficient adults.

Down's syndrome, a major cause of congenital mental retardation, is also the most common human birth defect. Down's syndrome occurs in about one out of every 800 newborns, with the incidence increasing markedly in the offspring of women over 35. Affecting an estimated one million Americans, it is the leading genetic cause of mental retardation and is associated with a shorter than average life expectancy. Other symptoms are heart and intestinal defects, problems with the immune and endocrine systems, and raft of tissue and skeletal deformities.

Over 90 percent of the individuals affected with Down's syndrome have an extra number 21 chromosome in all of their cells, giving each cell a total of 47 chromosomes rather than the normal 46. For this reason, the condition is also known as "Trisomy 21". Trisomy 21 results from nondisjunction or failure of chromosomes to separate sometime during either division of meiosis or mitosis. Most Down's syndrome individuals have trisomy 21, and conversely, in individuals who carry a translocation involving chromosome 21, and in mosaics who have both trisomic and normal cells, the characteristics of the syndrome are seen. There are, however, rare forms of Down syndrome in which only part of chromosome 21 is present in triplicate.

The present invention is further illustrated by the following examples, which are not intended to be limiting in any way.

EXEMPLIFICATION

Example 1

Chemical Induction of mGluR5- and Protein Synthesis-Dependent Long-Term Depression in Hippocampal Area CA1

Specific patterns of synaptic stimulation can induce long-term depression (LTD) in area CA1 of the hippocampus. The LTD depends on activation of metabotropic glutamate receptors (mGluRs) and rapid protein synthesis. As described herein this form of synaptic modification can be induced by brief application of the selective mGluR agonist (RS)-3,5-dihydroxyphenylglycine (DHPG). DHPG-LTD is a saturable form of synaptic plasticity, requires mGluR5, is mechanistically distinct from N-methyl-D-aspartate receptor (NMDAR)-dependent LTD, and shares a common expression mechanism with protein synthesis-dependent LTD evoked using synaptic stimulation. DHPG-LTD can be useful for biochemical analysis of mGluR5- and protein synthesis-dependent synaptic modification.

Introduction

Homosynaptic long-term depression (LTD) is a widely expressed form of synaptic plasticity in the brain. The best understood type of LTD is induced in hippocampal area CA1 by low-frequency synaptic stimulation (LFS) via an N-methyl-D-aspartate (NMDA) receptor-dependent rise in postsynaptic intracellular $Ca^{2+}$ and the activation of a protein phosphatase cascade (Bear and Abraham (1996)). Under the appropriate circumstances, pharmacological activation of NMDA receptors (NMDARs) can also induce this type of LTD. This "chem-LTD" approach has been useful for the biochemical characterization of the mechanism, revealing, for example, that NMDAR-dependent LTD is associated with dephosphorylation of the GluR1 subunit of the postsynaptic α-amino-3-hydroxy-5-methyl-4-isoxazolepropionic acid (AMPA) receptor (Lee et al. 1998).

Recent work has shown that mechanistically distinct types of LTD can also be induced in CA1 by other types of synaptic stimulation. For example, paired-pulse stimulation repeated at 1 Hz for 15 min (PP-LFS) induces LTD that is independent of NMDARs and requires activation of metabotropic glutamate receptors (mGluRs). This mGluR-dependent form of LTD is of particular interest because it also requires rapid translation of preexisting mRNA. A "chem-LTD" approach could be particularly useful for dissecting this novel mechanism. Indeed, reports from several groups indicate that transient activation of Group I mGluRs with the selective agonist (RS)-3,5-dihydroxyphenylglycine (DHPG) can induce LTD (Camodeca et al. 1999; Fitzjohn et al. 1999; Palmer et al. 1997). However, it is clear that not all protocols are equivalent; for example, some are effective only under conditions of low $Mg^{2+}$ and are partially dependent on NMDARs (Palmer et al. 1997; Schnabel et al. 1999).

Here we characterize a chemical induction protocol that reliably produces protein synthesis-dependent LTD (Huber et al. 2000). We show that mGluR5 is required for LTD induction and provide novel evidence that this chemically induced LTD shares a common saturable expression mechanism with LTD induced using PP-LFS. We anticipate that the method we describe here will be useful for understanding how mGluR activation regulates mRNA translation and the expression of synaptic LTD.

Methods

All animals were used in accordance with procedures approved by the Brown University Institutional Animal Care and Use Committee. Hippocampal slices were prepared from postnatal day 21-30 (P21-30) Long Evans rats (Charles River, Cambridge, Mass.) and mGluR5 knockout mice (Lu et al. 1997) as described previously (Huber et al. 2000). For most experiments, CA3 was removed immediately after sectioning. Slices recovered for 1-2 h at room temperature (rats) or at 30° C. (mice) in artificial cerebrospinal fluid (ACSF) containing (in mM) 124 NaCl, 5 KCl, 1.25 $NaH_2PO_4$, 26 $NaHCO_3$, 1 $MgCl_2$, 2 $CaCl_2$, and 10 dextrose, saturated with 95% $O_2$-5% $CO_2$. For recording, slices were placed in a submersion recording chamber and perfused with 30° C. ACSF at a rate of 2 ml/min.

Synaptically evoked field potentials (FPs) were recorded from area CA1 as described previously. Sharp microelectrode and whole cell voltage-clamp recordings were made using Axoclamp 2B and Axopatch 1D amplifiers (Axon Instruments), respectively. Sharp electrodes (80-120 M Ω) were filled with 3 M K-acetate and 10 mM KCl; patch pipettes (3-7 M Ω) were filled with (in mM) 134 K-gluconate, 6 KCl, 4 NaCl, 10 HEPES, 0.2 EGTA, 4 MgATP, 0.3 TrisGTP, and 14 phosphocreatine. The pH of the internal solution was adjusted to 7.25 with KOH, and the osmolarity was adjusted to 300 mOsm with $H_2O$ or sucrose. Only experiments in which there was less than a 15% change in series resistance were included in the analysis. Waveforms were filtered at 2 kHz and acquired and digitized at 10 kHz on a PC using Experimenter's Workbench (DataWave Systems, Boulder, Colo.).

Baseline responses were collected every 10-30 s using a stimulation intensity (10-30 μA; 0.2 ms) yielding 50-60% of the maximal response. Experiments in which there was a>5% drift in the response magnitude during the 20-min baseline period before DHPG or LFS were excluded from further analysis. All experiments with mGluR5 KO mice used wild-type littermates as controls and were performed blind to the genotype, later determined by Therion (Troy, N.Y.). LFS consisted of 900 pulses at 1 Hz. PP-LFS consisted of 900 pairs of stimuli (50-ms interstimulus interval) delivered at 1 Hz. In saturation experiments, stimulus duration was increased from 0.2 to 0.4 ms during PP-LFS.

The group data were analyzed as follows: 1) the initial slopes of the FPs and excitatory postsynaptic potentials (EPSPs), or the amplitude of the excitatory postsynaptic currents (EPSCs), for each experiment were expressed as percentages of the preconditioning or DHPG baseline average, 2) the time scale in each experiment was converted to time from the onset of conditioning or DHPG, and 3) the time-matched, normalized data were averaged across experiments and expressed in the text and figures as the means ±SE. Significant differences between groups were determined using an independent t-test or ANOVA performed on a 5-min average taken 1 h after LFS or DHPG application.

R,S-DHPG and D-2-amino-5-phosphonopentanoic acid (D-AP5) was purchased from Tocris (St. Louis, Mo.); all other chemicals were from Sigma Chemical (St Louis, Mo.). DHPG was prepared as a 100 times stock in $H_2O$, aliquoted and stored at −20° C. Fresh stocks were made once a week. A 10 times stock of AP5 was prepared in ACSF and stored at 4° C. These stocks were diluted in ACSF to achieve their final concentrations. Picrotoxin was dissolved directly into ACSF immediately before use.

Results

Figure 1:
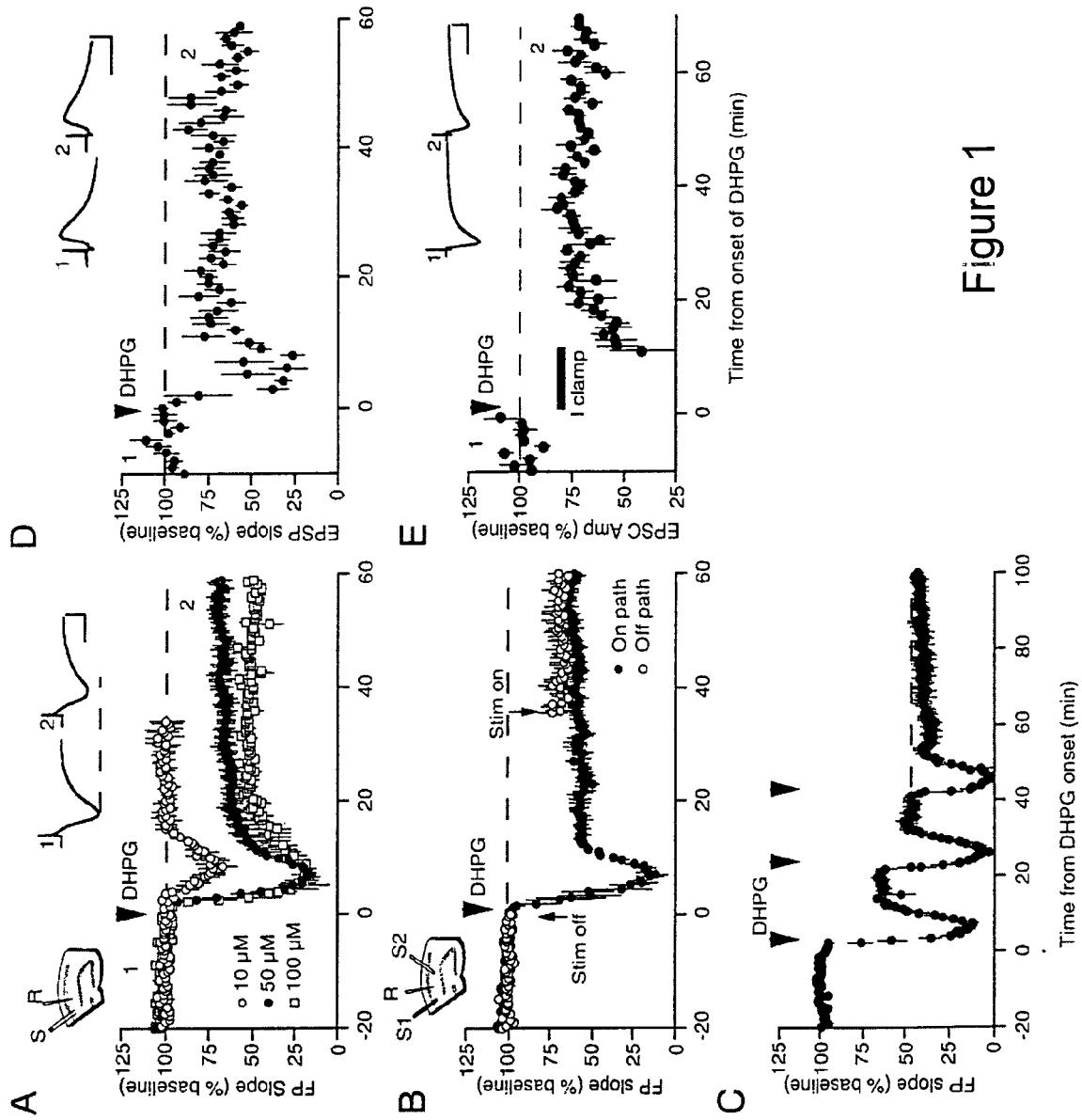

Application of DHPG for 5 min produced an acute, dose-dependent depression of evoked FPs (FIG. 1A). At concentrations ≧50 μM, the FP did not fully recover after drug wash out. Instead, the synaptic responses stabilized at a depressed level (50 μM: 69±5%, means ±SE, of pre-DHPG baseline; n=11; 100 μM: 48±1%; n=4). In all subsequent studies 50 μM, DHPG (5 min) was used to induce what we will refer to as DHPG-LTD. Application of another Group I mGluR agonist, quisqualic acid (5 min; 5 μM), also resulted in LTD (81±2%; n=4), confirming that the effect is not peculiar to DHPG. Two-pathway experiments (n=4), in which only one input was stimulated during DHPG, indicated that DHPG-LTD does not require concurrent synaptic stimulation (stimulated: 62±4%; unstimulated: 68±5%, P>0.2; FIG. 1B). DHPG-LTD also showed evidence of saturation; two applications of 50 μM DHPG were sufficient to produce maximal depression (FIG. 1C).

Intracellular recordings confirmed that the DHPG-LTD of FPs reflects diminished synaptic transmission. Both sharp electrode recording of EPSPs and whole cell voltage-clamp recording of EPSCs (recorded at −70 mV) revealed stable LTD (EPSP: 61±5%; n=6; FIG. 1D; EPSC: 69±5%; n=5; FIG. 1E). In contrast, there were no significant long-term changes in membrane potential, input resistance, or membrane excitability measured 1 h after DHPG (data not shown). Thus DHPG-LTD is a long-lasting modification of synaptic transmission.

The competitive NMDAR antagonist AP5 (50 μM) had no effect on the magnitude of DHPG-LTD as compared with interleaved control slices (AP5:83±3%, n=5; control: 85±3%, n=4; P>0.3; FIG. 2A). LTD induced with 5 μM quisqualic acid was also unaffected by AP5 (79±2%; n=3). Therefore LTD induced by pharmacological activation of Group I mGluRs under these experimental conditions does not require concurrent NMDAR activation.

To assess the involvement of mGluR5, the major Group I mGluR in area CA1 pyramidal neurons (Romano et al. 1995), DHPG-LTD was attempted in mice lacking this receptor. DHPG-LTD was absent in the mGluR5 homozygous mutants (98±3% measured 1 h after DHPG application; n=8; FIG. 2A). An intermediate amount of LTD was observed in heterozygous mutants (84±4%; n=6), as compared with wild-type littermate controls (77±2%; n=9; FIG. 2B). A one-way ANOVA revealed a significant effect of genotype [F(2,19)= 10.33, P<0.001]. A subsequent Tukey test revealed that both the wild-type and heterozygotes were significantly different from homozygotes (P<0.025). Although there is a trend for DHPG-LTD in the heterozygotes to be less than wildtypes, this is not significant (P=0.5). Thus DHPG-LTD strictly relies on mGluR5, and the presence of one allele for mGluR5 is sufficient for LTD induction. In contrast to DHPG-LTD, normal NMDAR-dependent LTD, induced with LFS, was observed in the homozygous mutants (87±2%; n=6; P>0.6; FIG. 2C) as compared with the wild type mice (89±5%; n=6). These results indicate that there are two distinct routes of LTD induction in area CA 1: one that relies on NMDARs and another on mGluR5.

The results from the mGluR5 knockouts indicate that the induction mechanisms of NMDAR-dependent LTD and DHPG-LTD are different. The next experiment was designed to test whether these two forms of LTD utilize similar expression mechanisms. Repeated episodes of LFS were delivered to saturate NMDAR-dependent LTD (FIG. 3A). DHPG then was then applied, and the magnitude of LTD was measured by renormalizing FP slope values to a pre-DHPG baseline. If NMDAR-dependent LTD and DHPG-LTD utilize a common expression mechanism, then previous saturation of NMDAR-dependent LTD should reduce or occlude DHPG-LTD. However, DHPG still significantly depressed synaptic responses (81±5% of pre-DHPG baseline; n=5; P<0.05; FIG. 3B), suggesting that NMDAR-dependent LTD and DHPG-LTD use distinct expression mechanisms.

The same approach was used to assess whether DHPG-LTD employs the same saturable expression mechanism as synaptically evoked mGluR-dependent LTD. PP-LFS in the presence of the NMDAR antagonist D-AP5 (50 μM) was used to saturate mGluR-dependent LTD, and DHPG (50 μM) was then applied to the slice (FIG. 3C). In contrast to the previous occlusion experiment, DHPG application after saturation of LTD with PP-LFS did not induce any further LTD (100±5% of pre-DHPG baseline; n=5; P>0.5; FIG. 3D). These results provide strong evidence that mGluR-LTD induced with DHPG and PP-LFS share common expression mechanisms.

Discussion

A number of different protocols have been introduced to induce homosynaptic LTD in CA1 (Berretta and Cherubini 1998; Camodeca et al. 1999; Dudek and Bear 1992; Fitzjohn et al. 1999; Huber et al. 2000; Kemp and Bashir 1999; Oliet et al. 1997; Overstreet et al. 1997; Palmer et al. 1997). Although mGluR involvement has been suggested for many of these, the constellation of findings is confusing and not entirely consistent with a single mGluR-dependent form of LTD. For example, it has been reported that application of 100 μM DHPG for 10 min to adult hippocampal slices elicits little LTD unless slice excitability is increased by removing $Mg^{2+}$ from the extracellular medium (Palmer et al. 1997; Schnabel et al. 1999). The resulting LTD is partially blocked by NMDAR antagonists. Moreover, PP-LFS in adult hippocampal slices can apparently elicit LTD via activation of either Group I mGluRs or activation of AMPA/kainate receptors (Kemp and Bashir 1999). In contrast, we recently demonstrated that in P21-30 rats, both PP-LFS and DHPG (50 μM, 5 min) induce LTD that is 1) independent of NMDAR activation, 2) blocked entirely by mGluR antagonists, and 3) dependent on a transient phase of mRNA translation (Huber et al. 2000). The latter finding is of particular importance, as this mGluR-LTD model should be useful for elucidating the regulation and function of dendritic protein synthesis, which may be defective in Fragile-X mental retardation (Jin and Warren 2000).

Because of the diverse effects of DHPG and PP-LFS, it could not be assumed that previous findings under different experimental conditions would apply to our model. Therefore it was necessary to characterize the protein synthesis-dependent form of mGluR-LTD. We have shown here that DHPG-LTD is a saturable form of synaptic plasticity, that it requires mGluR5, that it is mechanistically distinct from NMDAR-dependent LTD, and, importantly, that it shares a common saturable expression mechanism with the LTD evoked using PP-LFS. Because DHPG-LTD does not require concurrent synaptic stimulation, it is a form of "chem-LTD" (Lee et al. 1998) that should be useful for biochemical and biophysical studies.

References

Bear M F, and Abraham W C. Long-term depression in hippocampus. *Annu Rev Neurosci* 19:437-462, 1996.

Berretta N, and Cherubini E. A novel form of long-term depression in the CA1 area of the adult rat hippocampus independent of glutamate receptors activation. *Eur J Neurosci* 10:2957-2963, 1998.

Camodeca N, Breakwell N A, Rowan M J, and Anwyl R. Induction of LTD by activation of Group I mGluR in dentate gyrus in vitro. *Neuropharmacology* 38:1597-1606, 1999.

Dudek S M, and Bear M F. Homosynaptic-long-term depression in area CA1 of hippocampus and effects of N-methyl-D-aspartate receptor blockade. *Proc Natl Acad Sci USA* 89:4363-4367, 1992.

Fitzjohn S M, Kingston A E, Lodge D, and Collingridge G L. DHPG-induced LTD in area CA1 of juvenile rat hippocampus; characterisation and sensitivity to novel mGlu antagonists. *Neuropharmacology* 38:1577-1584, 1999.

Huber K M, Kayser M S, and Bear M F. Role for rapid dendritic protein synthesis in hippocampal mGluR-dependent long-term depression. *Science* 288:1254-1257, 2000.

Jin P, and Warren S T. Understanding the molecular basis of Fragile X syndrome. *Hum Mol Genet* 9:901-908, 2000.

Kemp N, and Bashir Z I. Induction of LTD in the adult hippocampus by the synaptic activation of AMPA/kainate and metabotropic glutamate receptors. *Neuropharmacology* 38:495-504, 1999.

Lee H K, Kameyama K, Huganir R L, and Bear M F. NMDA induces long-term synaptic depression and dephosphorylation of the GluR1 subunit of AMPA receptors in hippocampus. *Neuron* 21:1151-1162, 1998.

Lu Y M, Jia Z, Janus C, Henderson J T, Gerlai R, Wojtowicz J M, and Roder J C. Mice lacking metabotropic glutamate receptor 5 show impaired learning and reduced CA1 long-term potentiation (LTP) but normal CA3 LTP. *J Neuroscience* 17:5196-5205, 1997.

Oliet S H, Malenka R C, and Nicoll R A. Two distinct forms of long-term depression coexist in CA1 hippocampal pyramidal cells. *Neuron* 18:969-982, 1997.

Overstreet L S, Pasternak J F, Colley P A, Slater N T, and Trommer B L. Metabotropic glutamate receptor mediated long-term depression in developing hippocampus. *Neuropharmacology* 36:831-844, 1997.

Palmer M J, Irving A J, Seabrook G R, Jane D E, and Collingridge G L. The group I mGlu receptor agonist DHPG induces a novel form of LTD in the CA1 region of the hippocampus. *Neuropharmacology* 36:1517-1532, 1997.

Romano C, Sesma M A, McDonald C T, O'Malley K, van der Pol A, and Olney J W. Distribution of metabotropic glutamate receptor mGluR5 immunoreactivity in rat brain. *J Comp Neurol* 355:455-469, 1995.

Schnabel R, Kilpatrick I C, and Collingridge G L. An investigation into signal transduction mechanisms involved in DHPG-induced LTD in the CA1 region of the hippocampus. *Neuropharmacology* 38:1585-1596, 1999.

Example 2

Internalization of Ionotropic Glutamate Receptors in Response to mGluR Activation Activation of Group I mGluR I metabotropic glutamate receptors (mGluRs) stimulates dendritic protein synthesis and long-term synaptic depression (LTD), but it remains unclear how these effects are related. Here we provide evidence that a consequence of mGluR activation in the hippocampus is the rapid loss of both AMPA and NMDA receptors from synapses. Like mGluR-LTD, the stable expression of this change requires protein synthesis. These data suggest that expression of mGluR-LTD is at least partly postsynaptic, and that a functional consequence of dendritic protein synthesis is the regulation of glutamate receptor trafficking.

Introduction

Two mechanistically distinct forms of homosynaptic long-term depression (LTD) coexist in the hippocampus. Induction of one form depends on activation of N-methyl-D-aspartate receptors (NMDARs) and postsynaptic protein phosphatases, and induction of the other depends on activation of postsynaptic Group I metabotropic glutamate receptors (mGluRs) and the local translation of dendritic mRNA[1]. There is strong support for the idea that NMDAR-dependent LTD (NMDA-LTD) is a consequence of reduced synaptic expression of α-amino-3-hydroxy-5-methylisoxazole-4-propionate receptors (AMPARs)[2-7]. Less is known about expression of mGluR-dependent LTD (mGluR-LTD), although a presynaptic mechanism has been suggested[8,9].

Until recently, progress on mGluR-LTD has been hampered by the lack of a reliable synaptic induction protocol. An alternative method has been to transiently activate Group I mGluRs with the selective agonist (R,S)-3,5-dihydroxyphenylglycine (DHPG)[10-13]. In hippocampal slices, DHPG (50 µM, 5 min) induces LTD in that requires protein synthesis[13], and that seems to use the same saturable expression mechanism as mGluR-LTD evoked with patterned synaptic activity[14]. Therefore, we used this chemical induction protocol on hippocampal neurons in culture and in slices to investigate the possibility that mGluR-LTD is expressed as a change in postsynaptic glutamate receptor expression.

Results

1) DHPG Stimulates Internalization of AMPARs

To examine the effect of mGluR activation on AMPARs expressed on the surface of hippocampal neurons, we used an acid-strip immunocytochemical staining protocol[3]. Surface receptors on living cultured hippocampal neurons were labeled with antibodies directed against the extracellular N-terminus of the GluR1 subunit. The cells were treated with either DHPG (50 µM, 5 min) or control medium and, after various intervals, the remaining surface antibodies were stripped away with an acetic acid wash. The neurons were fixed, and immunocytochemistry was done under membrane-permeabilizing conditions to detect antibodies bound to internalized AMPARs. All analyses were performed blind, without experimenter knowledge of the treatment conditions.

DHPG application for 5 minutes stimulated a greater than 2-fold increase in internalized GluR1 puncta that was observed as early as 15 minutes after treatment onset (puncta per 10 µm of dendrite, control, 0.62±0.09, n=65 cells; DHPG, 1.44±0.17, n=60 cells; p<0.0002) and persisted for at least 1 hour (control, 0.58±0.08, n=42 cells; DHPG, 1.14±0.15, n=38 cells; FIGS. 4A and B). The increased internalization of GluR1 was a specific consequence of activating Group I mGluRs, as it was completely blocked by the mGluR antagonist LY344545 (ref. 15; 100 µM; control, 0.42±0.10, n=15; DHPG, 1.39±0.34, n=14; LY344545 alone, 0.32±0.08, n=13; DHPG+LY344545, 0.29±0.04, n=17; FIG. 4C). In contrast, the NMDAR antagonist 2-amino-5-phosphonovaleric acid (APV, 50 µM) had no effect (control, 0.74±0.19, n=7; DHPG, 1.49±0.22, n=10; DHPG+APV, 1.51±0.3, n=10).

Stable expression of mGluR-LTD requires dendritic protein synthesis[13]. We found that pretreatment of cultures with the mRNA translation inhibitor cycloheximide (chx, 60 µM, applied 15 min before DHPG) also significantly inhibited the DHPG-induced increase in internalized GluR1 measured at 60 minutes (control, 0.85±0.14, n=24; DHPG, 1.5±0.27, n=20; DHPG+chx, 1.02±0.12, n=25, different from DHPG alone at p<0.03, FIG. 4D). A mechanistically distinct protein synthesis inhibitor, anisomycin, also blocked mGluR-stimulated endocytosis (data not shown). Neither cycloheximide nor anisomycin had any significant effect on basal levels of internalized puncta (control+chx, 0.76±0.09, n=10, FIG. 4D).

2) Surface AMPARs are Lost Following DHPG Treatment

We next determined if the DHPG-induced increase in internalized AMPARs is accompanied by a net decrease in surface-expressed receptor clusters at synapses. At various intervals after DHPG washout, cells were fixed and surface GluR2 or GluR1 was labeled with N-terminal antibodies without permeabilization. The cultures were then permeabilized, and synapses were labeled using an antibody against the presynaptic marker synapsin I or synaptophysin coupled to the appropriate secondary antibody. Under control conditions, most synapses were immunoreactive for AMPAR clusters (GluR2, 80.6±9.0%; n=10 cells, 200 synapses, FIGS. 5A-D; GluR1, 72.5±4.7%; n=15 cells, 225 synapses; FIGS. 5E and F).

The percentage of synapses with AMPAR clusters was dramatically reduced by DHPG treatment. Only 40.8±11% of synapses had surface staining for GluR2 (n=10 cells, 200 synapses; p<0.03) measured 1 hour after treatment (FIGS. 5G-I). Similar results were obtained in additional experiments with GluR1 (29.3±5.4% GluR1-positive synapses 15 min after DHPG treatment, n=14 cells, 210 synapses; 20.0±12.0% GluR1-positive synapses 60 min after DHPG treatment, n=15 cells, 225 synapses; FIGS. 5J and K).

Pretreatment of cultures with cycloheximide (60 μM, applied 15 min before DHPG) inhibited the DHPG-induced decrease in synaptic GluR1 clusters measured at 60 minutes (synapses with GluR1, 55.7±5.1%, n=15 cells, 225 synapses; p<0.05 versus DHPG alone; FIG. 5K). However, the number of GluR1-positive synapses decreased 15 minutes after DHPG onset in the presence of the inhibitor (synapses with GluR1, 37.8±3.8%, n=15 cells, 225 synapses; FIG. 5J). These findings suggest that protein synthesis is involved in determining the fate of internalized receptors, but not in the initial endocytosis stimulated by mGluR activation.

Figure 6:
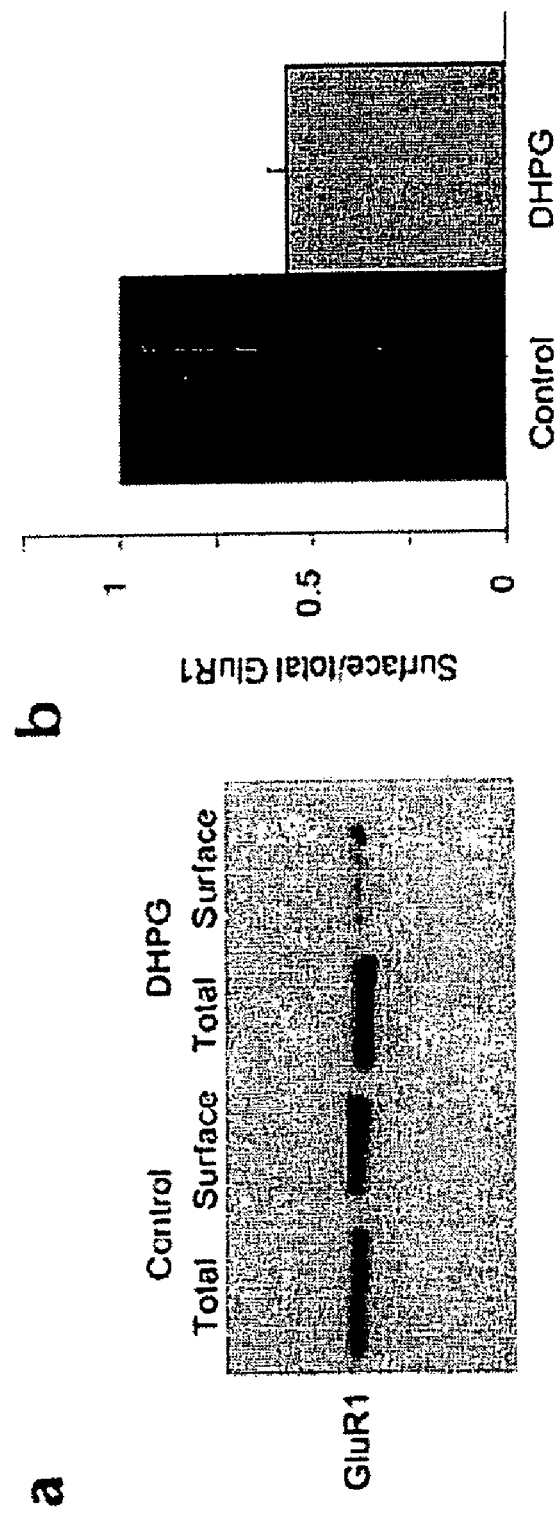

To confirm the effect of mGluR activation on surface AMPARs using an alternative approach, we treated high-density cultures with DHPG (50 μM, 5 min) or control medium and surface receptors were labeled with biotin 60 minutes later. Biotinylated receptors were precipitated and the ratio of surface to total GluR1 was determined by quantitative western blotting. This biochemical analysis confirmed that surface AMPARs are reduced by DHPG treatment to only 56.8±4.0% of the value in control cultures (n=4 in each treatment group; p<0.01; FIG. 6).

3) DHPG Application Reduces mEPSC Frequency

Figure 7:
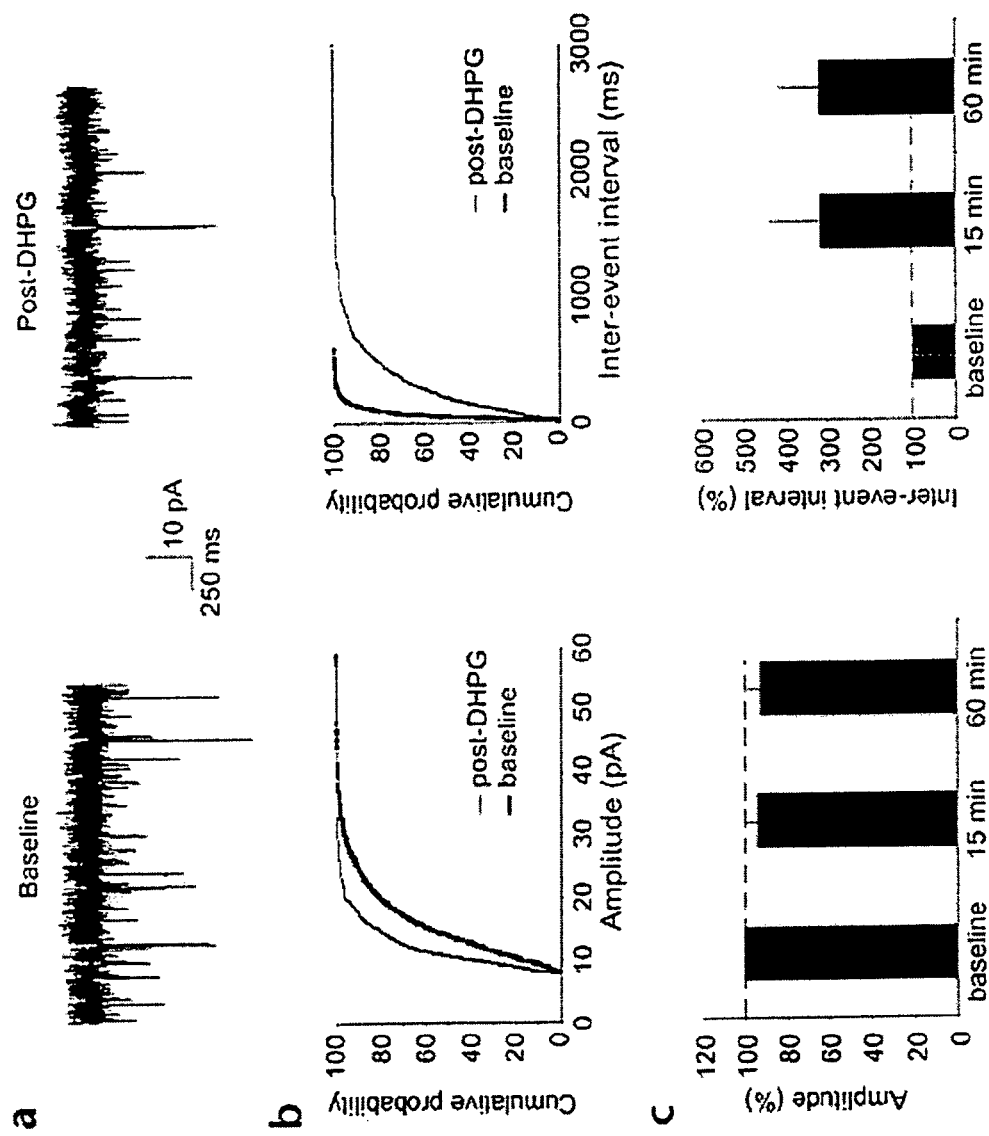

The immunocytochemical and biochemical experiments suggest that DHPG treatment is likely to have a significant effect on AMPAR-mediated synaptic transmission in cultured neurons. To investigate this possibility directly, we examined the effect of DHPG on AMPAR-mediated mEPSCs. As reported for other manipulations that stimulate receptor internalization (for example, see ref. 16), we observed a significant decrease in the frequency of mEPSCs. The inter-event interval was 315% of baseline at 15 min after DHPG treatment (n=11 cells, p<0.05) and 319% of baseline at 60 minutes (n=9 cells, p<0.002; FIG. 7).

In addition to the change in frequency, there was also a trend toward attenuated mEPSC amplitude at 15 (94.2% baseline; n=11 cells) and 60 (92.2% baseline; n=9 cells; FIG. 7) minutes following DHPG, but this effect did not achieve statistical significance. Considered together with the imaging and biochemical results, the most straightforward interpretation of the mEPSC data is that DHPG silences a discrete population of synapses because its entire complement of AMPARs is internalized.

4) Surface NMDARs are Lost Following DHPG Treatment

NMDAR activation has been reported to stimulate a loss of synaptic AMPARs without affecting NMDARs[2]. To determine if mGluR-stimulation affects NMDAR clusters, cells were treated with DHPG, fixed and stained with an N-terminal antibody for the NR1 subunit of the NMDAR under non-permeabilizing conditions. The cells were then permeabilized and synapses were labeled using an antibody against synapsin I. In control neurons, 67±4% of synapses (n=20 cells, 300 synapses) contained NR1 immunoreactive puncta (FIGS. 8A-D and G). Following DHPG treatment, the percentage of NR1-positive synapses was reduced to 28±6% at 15 minutes (n=16 cells, 240 synapses, p<0.003) and 21±3% at 60 minutes (n=19 cells, 285 synapses; FIGS. 8E and G). As was the case for AMPARs, the change in surface NR1 clusters following DHPG was significantly attenuated at 60 minutes when the cultures were treated with cycloheximide (42+5% NR1-labeled at 60 min; n=20 cells, 300 synapses; p<0.05 versus DHPG alone; FIG. 8G).

The loss of NMDARs from synapses following DHPG was surprising. To rule out the possibility of nonspecific changes in the postsynaptic neurons, we monitored changes in the distribution of synaptic $GABA_A$ receptors using an antibody against the N-terminal of the $\beta_1$ subunit. Unlike synapses with glutamate receptors, -DHPG had no effect on the percentage of synapsin-labeled puncta with $GABA_A\beta_1$ clusters (control, 11.8±4%, n=10 cells, 150 synapses; 60 min after DHPG treatment, 10.9±2%, n=10; data not shown). To corroborate the loss of surface NMDARs following DHPG, high-density cultures were treated with DHPG (50 μM, 5 min, n=5), DHPG+cycloheximide (60 μM; n=4), or control medium (n=5), and surface NMDARs were labeled with biotin 60 minutes later. Biotinylated receptors were precipitated and the ratio of surface to total NR1 was determined by quantitative western blotting (FIGS. 8H and I). This analysis confirmed that surface NMDARs are significantly reduced by DHPG treatment to 32.3±8.2% of the value in control cultures, and that this change is inhibited by cycloheximide (79.1±14.5% of control; FIG. 8I).

5) LTD of NMDAR-EPSCs

The loss of synaptic NR1 clusters clearly distinguishes the effect of DHPG from other treatments that selectively affect AMPARs[2,17-19]. Thus, our data suggest that in addition to the depression of AMPAR-mediated synaptic transmission, induction of mGluR-LTD should also affect transmission mediated by NMDARs. To test this hypothesis, we chemically induced LTD in hippocampal slices from postnatal day 21-28 (P21-28) rats with DHPG[14] as we monitored NMDAR mediated excitatory postsynaptic currents (EPSCs) in CA1 neurons voltage clamped at +40 mV, as described previously[20]. These experiments revealed that application of DHPG (5 min) produced a dose-dependent LTD of NMDAR-EPSCs (EPSC amplitude 30 minutes after DHPG treatment as percent of baseline, 50 μM, 70.7±2.9, n=3, p<0.05; 100 μM: 57.7±1.0, n=5; different from baseline at p<0.00005, paired t-test; FIG. 9A.

As an additional test for an mGluR-induced loss of NMDAR function, we examined the effects of 100 μM DHPG (5 min) on currents evoked by NMDA applied near the proximal portion of the primary apical dendrite (FIG. 9B). Significant depression of NMDAR currents occurred (percent baseline at 50-60 min after DHPG treatment, DHPG, 61.1±12.0, n=7; control, 97.3±9.4; n=7; p<0.05); however, the time course of this change was much slower than that observed for synaptically evoked EPSCs. Unlike the EPSCs, which depressed immediately, the NMDA-evoked currents transiently potentiated (as described previously with the agonist 1-amino-cyclopentane-1,3 dicarboxylic acid (ACPD)[10,21]) and then slowly decreased over the course of an hour. The early LTD of EPSCs could be accounted for by a presynaptic mechanism or by the rapid dispersal of synaptic NMDARs (without immediate internalization). Migration of NMDARs within the membrane has been demonstrated both in cultured cells[22] and in slices[23]. Regardless of the early consequences, however, the parallel depression of NMDAR EPSCs and NMDA-evoked responses 60 minutes after DHPG treatment is consistent with an eventual reduction in surface NMDAR expression during mGluR-LTD.

Discussion

Our data demonstrate that activation of Group I mGluRs in cultured hippocampal neurons stimulates internalization of synaptic AMPA and NMDA receptors, and that the stable expression of these changes is sensitive to protein synthesis inhibitors. The same DHPG treatment (50 µM, 5 min) in hippocampal slices stimulates mGluR-LTD that depends upon postsynaptic mRNA translation[13] and, as we now show, is expressed as a change in NMDAR- as well as AMPAR-mediated transmission. Thus, removal of synaptic glutamate receptors is a candidate mechanism for the expression of mGluR-LTD in the hippocampus. This notion is consistent with the finding that cerebellar LTD, which is also triggered by activation of Group I mGluR, requires postsynaptic endocytosis of AMPARs[24].

Hippocampal mGluR-LTD was previously shown to be associated with a reduced frequency of spontaneous and evoked postsynaptic responses which, according to the traditional assumptions of quantal analysis, suggested a presynaptic expression mechanism[8,9]. However, these data are also consistent with 'synaptic silencing,' arising from the complete loss of receptors at an activated synapse[16,17,25].

Similar to what we observe following mGluR activation, NMDA-LTD is associated with a reduced expression of postsynaptic AMPARs (and a decreased frequency of spontaneous excitatory postsynaptic currents[2]). In principle, the two routes of LTD induction could converge on a common saturable expression mechanism at the same synapses; however, this hypothesis is at odds with the finding that mGluR-LTD and NMDA-LTD are not mutually occluding[9,14]. An alternative is that mGluRs and NMDARs regulate separate populations of AMPARs, perhaps at distinct populations of synapses.

Several previous studies suggested that synaptic NMDARs are relatively static in comparison to AMPARs[4,19,27]. However, we find that both NMDARs and AMPARs are internalized with a similar time-course (<15 min) following DHPG treatment. Rapid endocytosis of NMDARs has also been demonstrated in immature cortical cultures under basal conditions[28]. This receptor internalization was inhibited by the binding of the postsynaptic density protein PSD95 to the C-terminus of the NR2B subunit. Thus, a potential mechanism for DHPG-stimulated NMDAR endocytosis could involve regulation of the interaction of PSD95 and NR2B.

Besides their obvious relevance to hippocampal mGluR-LTD, we suggest our findings may be of additional significance. First, we show a unique role for protein synthesis that, considered with previous findings[13,26,29], is likely to occur in the postsynaptic neuron as a specific consequence of synaptic activity. Using glutamate receptor trafficking as an assay, this preparation should be very useful for dissecting the molecular mechanisms that couple mGluR activation to dendritic mRNA translation regulation. Second, the loss of ionotropic receptors on hippocampal neurons following DHPG is reminiscent of what happens at the neuromuscular junction before synapse elimination[30], and Group I mGluRs have recently been implicated in the loss of climbing fiber synapses in the developing cerebellum[31]. Thus, the model we describe here should be useful for testing the long-standing hypothesis that mGluRs and the mechanisms of LTD are involved in activity-dependent synapse elimination in the cerebral cortex[32,33].

Methods

1) Acid Strip Immunocytochemical Protocol

Low-density cultures of rat hippocampal neurons were made as previously described[34]. All rats were housed in the Brown University Animal Care Facility and all procedures were approved by Brown University Animal Care and Use Committee. Briefly, the hippocampus was removed from E18 rat fetuses, trypsinized (0.25%), dissociated by trituration, and plated onto poly-L-lysine (1 mg/ml) coated glass coverslips (80,000 cells/ml) for 4 h. The coverslips were then transferred to dishes containing a monolayer of glial cells in growth medium and the neurons were allowed to mature for 14-22 days. Surface AMPARs were labeled on live cells with an antibody directed against the extracellular N-terminus of the GluR1 subunit (amino acids 271-285; 5 µg per ml; Oncogene Research, San Diego, Calif., and a gift of R. Huganir). The neurons were then treated with a specific agonist of the Group I mGluRs DHPG, 50 µM in medium) or control medium for 5 min. Ten or fifty-five minutes following treatment, the cells were chilled in 4° C. Tris-buffered saline (TBS) to stop endocytosis, and then exposed to 0.5 M NaCl/ 0.2 M acetic acid (pH 3.5) for 4 min on ice to remove antibody bound to extracellular GluR1. Cultures were rinsed and fixed in 4% paraformaldehyde with 4% sucrose. Nonspecific staining was blocked and cells were permeabilized in TBS containing 0.1% Triton-X, 4% goat serum and 2% BSA. Internalized primary antibody was made visible by incubation with a Cy3-labeled secondary antibody for 1 h (1:300). In the initial studies, treatments included 1 µM tetrodotoxin and 1 µM ω-conotoxin to limit depolarization-induced neurotransmitter release. We later found that identical results were obtained without ω-conotoxin, so this treatment was subsequently omitted.

2) Immunocytochemical Localization of Synaptic Receptors

Following experimental treatment, low-density cultures were fixed in 4% paraformaldehyde with 4% sucrose for 5 min. Cultures were rinsed in PBS and then blocked in PBS with 20% fetal bovine serum for 1 h. Cultures were stained with N-terminal receptor antibodies overnight at 4° C. (GluR2, 1:100, Chemicon, Ternecula, California; GluR1, 1:100, gift of R. Huganir; NR1, 1:500, Chemicon MAB363; $GABA_A\beta_1$, 1:100 Santa Cruz Biologicals, Santa Cruz, Calif.). Cultures were then rinsed in blocking buffer containing 0.1% Triton-X for 20 min and exposed to antibodies directed against presynaptic proteins (synapsin 1, 1:1000, Chemicon; synaptophysin, 1:100, Boehringer Manheim, Irvine, Calif.) for 1 h at room temperature. Cultures were then rinsed and exposed to the appropriate fluorescent secondary antibodies (Jackson Immunoresearch, West Grove, Pa.).

3) Analysis of Immunocytochemical Data

Microscopy was performed with a Nikon E800 microscope using a 60×1.4 NA objective (Melville, N.Y.). Fluorescence images were collected with a Sensys cooled CCD camera and analyzed using IP-Labs software. Additional images were collected with a Olympus Flowview confocal microscope with a 60×1.2 NA objective. All analyses were performed blind to the stimulation history of the culture. Microscopic fields had 1-3 neurons displaying smooth soma and generally healthy morphology with multiple distinct processes. Immunofluorescence was analyzed along the proximal 50 µm of 3 or more dendrites per neuron. Immunoreactive puncta were defined as discrete points along the dendrite with fluorescence intensity twice the background staining of the neuron. Five cells were analyzed per culture and 3-6 cultures were analyzed per condition. Separate controls were performed with each experiment and a Student's t-test was used to determine statistical significance. Data are expressed as puncta per 10 μm of dendrite unless stated otherwise.

4) Biochemical Measurements of Surface Expressed Receptors

Biotinylation experiments were performed as previously described[35]. Briefly, 2-week-old high-density cultured hippocampal neurons were treated with either control medium or 50 μM DHPG for 5 min, and incubated for 1 h at 37° C. to allow endocytosis to occur. The sister cultures were placed on ice to stop endocytosis and washed two times with ice-cold artificial cerebrospinal fluid (ACSF) containing 124 mM NaCl, 5 mM KCl, 1.25 mM $NaH_2PO_4$, 26 mM $NaHCO_3$, 0.8 mM $MgCl_2$, 1.8 mM $CaCl_2$, 10 mM dextrose, and saturated with 95% $O_2$, 5% $CO_2$. Cultures were then incubated with ACSF containing 1 mg/ml Sulfo-NHS-LC-Biotin (Pierce Chemical Company, Rockford, Ill.) for 30 min on ice. Cultures were rinsed in TBS to quench the biotin reaction. Cultures were lysed in 300 μl of modified RIPA buffer (1% Triton X-100, 0.1% SDS, 0.5% deoxycholic acid, 50 mM $NaPO_4$, 150 mM NaCl, 2 mM EDTA, 50 mM NaF, 10 mM sodium pyrophosphate, 1 mM sodium orthovanadate, 1 mM PMSF, and 1 mg/ml leupeptin). The homogenates were centrifuged at 14,000×g for 15 min at 4° C. Fifteen microliters (5%) of the supernatant were removed to measure total GluR1 or NR1; 200 μl (66.67%) of the remaining supernatant was incubated with 100 μl of 50% Neutravidin agarose (Pierce Chemical Company) for 3 h at 4° C., washed 3 times with RIPA buffer, and bound proteins were resuspended in 40 μl of SDS sample buffer and boiled. Quantitative western blots were performed on both total and biotinylated (surface) proteins using anti-GluR1 C-terminal (1:1000, Upstate Biotechnology, Lake Placid, N.Y.) and anti-NR1 N-terminal antibodies (1:1000, Chemicon). Immunoreactive bands were visualized by enhanced chemiluminescence (ECL, Amersham, Piscataway, N.J.) captured on autoradiography film (Amersham Hyperfilm ECL). Digital images, produced by densitometric scans of autoradiographs on a ScanJet IIcx (Hewlett Packard, Palo Alto, Calif.) with DeskScan II software (Hewlett Packard), were quantified using NIH Image 1.60 software. The surface/total ratio was calculated for each culture, and treatment groups were compared using a paired t-test. Control experiments confirmed that the intracellular protein actin was not biotinylated in this assay. For display purposes, the data are expressed as the ratio of DHPG to control values.

5) mEPSC Recordings and Analysis

Cultured hippocampal cells at room temperature were superfused at 1 ml/min in medium consisting of 140 mM NaCl, 3.5 mM KCl, 10 mM HEPES, 20 mM glucose, 1.8 mM $CaCl_2$, 0.8 mM $MgCl_2$, 0.05 mM picrotoxin, 0.001 mM TTX, and pH was adjusted to 7.4 with NaOH. Patch electrodes (4-5 m Ω) were filled with 116 mM Kgluconate, 6 mM KCl, 20 mM HEPES, 0.5 mM EGTA, 2 mM NaCl, 4 mM Mg-ATP, 0.3 mM Na-GTP, 10 mM sodium phosphocreatine, adjusted to pH 7.3 and osmolarity ~300 mM. Cells were voltage-clamped at −60 mV (near the resting membrane potential of the cells), and mEPSCs were amplified using the Axopatch ID amplifier. Recordings were filtered at 2 kHz, digitized at 10 kHz, and stored on a computer using Experimenter's Workbench (DataWave Systems, Boulder, Colo.) and on videotape. Series and input resistances were monitored throughout the experiment and only those cells stable (<15% change) in these parameters were included in the analysis. Average input resistance was ~600 M Ω and average series resistance was ~15 M Ω. Events were detected off-line using an automatic detection program (MiniAnalysis, Synaptosoft, Decatur, Georgia) with a detection threshold set at a value greater than at least two standard deviations of the noise values. The detection threshold remained constant for the duration of each experiment. Only events with a monotonic rise time and exponential decay were included in the analysis. Inter-event interval and mEPSC amplitude were compared during a 10-min baseline period and in 10-min windows 15 and 60 minutes after 50 μM DHPG application for 5 min. Due to non-normal distributions of mEPSC parameters, statistics were performed using the Wilcoxon signed-ranks test and significance was placed at p<0.05.

6) Hippocampal Slice Physiology

Hippocampal slices were prepared from P21-30 Long Evans rats (Charles River, Cambridge, Mass.) as described previously[13,14]. Slices recovered for 1-2 h at room temperature in artificial cerebrospinal fluid (ACSF) containing 124 mM NaCl, 5 mM KCl, 1.25 mM $NaH_2PO_4$, 26 mM $NaHCO_3$, 1 mM $MgCl_2$, 2 mM $CaCl_2$, 10 mM dextrose, saturated with 95% $O_2$, 5% $CO_2$. For recording, slices were placed in a submersion recording chamber and perfused with 30° C. ACSF at a rate of 2 ml/min.

Synaptically evoked-NMDAR-mediated EPSCs were recorded from area CA1 as described previously for visual cortex[20]. NMDA-evoked currents were examined by picospritzing 1 mM NMDA (made in ACSF), applied for 3.5-12.5 ms, near the proximal portion of the primary apical dendrite. NMDA-evoked currents were elicited once every two minutes. Stimulation intensity or picospritz pulse duration/pressure were adjusted to evoke an inward current with amplitude of 50 pA or greater.

References

Bear, M. F. & Linden, D. J. in *Synapses* (eds. Cowan, W. M., Sudhoff, T. C. & Stevens, C. F.) 455-517 (The Johns Hopkins University Press, Baltimore, Md., 2001).

Carroll, R. C., Lissin, D. V., von Zastrow, M., Nicoll, R. A. & Malenka, R. C. Rapid redistribution of glutamate receptors contributes to long-term depression in hippocampal cultures. *Nat. Neurosci.* 2, 454-460 (1999).

Carroll, R. C. et al. Dynamin-dependent endocytosis of ionotropic glutamate receptors. *Proc. Natl. Acad. Sci. USA* 96, 14112-14117 (1999).

Luischer, C. et al. Role of AMPA receptor cycling in synaptic transmission and plasticity. *Neuron* 24, 649-658 (1999).

Liao, D., Zhang, X., O'Brien, R., Ehlers, R. O. & Huganir, R. L. Regulation of morphological postsynaptic silent synapses in developing hippocampal neurons. *Nat. Neurosci.* 2, 37-43 (1999).

Man, H.-Y. et al. Regulation of AMPA receptor-mediated synaptic transmission by clathrin-dependent receptor internalization. *Neuron* 25, 649-662 (2000).

Heynen, A. J., Quinlan, E. M., Bae, D. C. & Bear, M. F. Bidirectional, activity-dependent regulation of glutamate receptors in the adult hippocampus in vivo. Neuron 28, 527-536 (2002).

Bolshakov, V. Y. & Siegelbaum, S. A. Postsynaptic induction and presynaptic expression of hippocampal long-term depression. *Science* 264, 1148-1152 (1994).

Oliet, S. H., Malenka, R. C. & Nicoll, R. A. Two distinct forms of long-term depression coexist in CA1 hippocampal pyramidal cells. *Neuron* 18, 969-982 (1997).

Palmer, M. J., Irving, A. J., Seabrook, G. R., Jane, D. E. & Collingridge, G. L. The group I mGlu receptor agonist DHPG induces a novel form of LTD in the CA1 region of the hippocampus. *Neuropharmacology* 36, 1517-1532 (1997).

Camodeca, N., Breakwell, N. A., Rowan, M. J. & Anwyl, R. Induction of LTD by activation of group I mGluR in the dentate gyrus in vitro. *Neuropharmacology* 38, 1597-1606 (1999).

Fitzjohn, S. M., Kingston, A. E., Lodge, D. & Collingridge, G. L. DHPG-induced LTD in area CA1 of juvenile rat hippocampus; characterisation and sensitivity to novel mglu receptor antagonists. *Neuropharmacology* 38, 1577-1583 (1999).

Huber, K. M., Kayser, M. S. & Bear, M. F. Role for rapid dendritic protein synthesis in hippocampal mGluR-dependent long-term depression. *Science* 288, 1254-1256 (2000).

Huber, K. M., Roder, J. & Bear, M. F. Chemical induction of mGluR- and protein synthesis-dependent long-term depression in hippocampal area CA1. *J. Neurophysiol.* 86, 321-325 (2001).

Doherty, A. et al. A novel, competitive mGluR5 receptor antagonist (LY344545) blocks DHPG-induced potentiation of NMDA responses but not the induction of LTP in rat hippocampal slices. *Br. J. Pharmacol.* 131, 239-244 (2000).

Noel, J. et al. Surface expression of AMPA receptors in hippocampal neurons is regulated by an NSF-dependent mechanism. *Neuron* 23, 365-376 (1999).

Beattie, E. C. et al. Regulation of AMPA receptor endocytosis by a signaling mechanism shared with LTD. *Nat. Neurosci.* 3, 1291-1300 (2000).

Man, Y. H. et al. Regulation of AMPA receptor-mediated synaptic transmission by clathrin-dependent receptor internalization. *Neuron* 25, 649-662 (2000).

Ehlers, M. D. Reinsertion or degradation of AMPA receptors determined by activity-dependent endocytic sorting. *Neuron* 28, 511-525 (2000).

Philpot, B. D., Sekhar, A. K., Shouval, H. Z. & Bear, M. F. Visual experience and deprivation bidirectionally modify the composition and function of NMDA receptors in visual cortex. *Neuron* 29, 157-169 (2001).

Cohen, A. S. & Abraham, W. C. Facilitation of long-term potentiation by prior activation of metabotropic glutamate receptors. *J. Neurophysiol.* 76, 953-962 (1996).

Ehlers, M. D., Tingley, W. G. & Huganir, R. L. Regulated subcellular distribution of the NR1 subunit of the NMDA receptor. *Science* 269, 1734-1737 (1995).

Benke, T. A., Jones, O. T., Collingridge, G. L. & Angelides, K. J. N-Methyl-D-aspartate receptors are clustered and immobilized on dendrites of living cortical neurons. *Proc. Natl. Acad. Sci. USA* 90, 7819-7823 (1993).

Wang, Y. T. & Linden, D. J. Expression of cerebellar long-term depression requires postsynaptic clathrin-mediated endocytosis. *Neuron* 25, 635-647 (2000).

Luthi, A. et al. Hippocampal LTD expression involves a pool of AMPARs regulated by the NSF-GluR2 interaction. *Neuron* 24, 389-399 (1999).

Kauderer, B. S. & Kandel, E. R. Capture of a protein synthesis-dependent component of long-term depression. *Proc. Natl. Acad. Sci. USA* 97, 13342-13347 (2000).

Lin, J. W. et al. Distinct molecular mechanisms and divergent endocytotic pathways of AMPA receptor internalization. *Nat. Neurosci.* 3, 1282-1290 (2000).

Roche, K. W. et al. Molecular determinants of NMDA receptor internalization. *Nat. Neurosci.* 4, 794-802 (2001).

Weiler, I. J. & Greenough, W. T. Metabotropic glutamate receptors trigger postsynaptic protein synthesis. *Proc. Natl. Acad. Sci. USA* 90, 7168-7171 (1993).

Balice-Gordon, R. J. & Lichtman, J. W. Long-term synapse loss induced by focal blockade of postsynaptic receptors. *Nature* 372, 519-524 (1994).

Ichise, T. et al. MGluR1 in cerebellar Purkinje cells essential for long-term depression, synapse elimination, and motor coordination. *Science* 288, 1832-1835 (2000).

Dudek, S. M. & Bear, M. F. A biochemical correlate of the critical period for synaptic modification in the visual cortex. *Science* 246, 673-675 (1989).

Bear, M. F. & Rittenhouse, C. D. A molecular basis for induction of ocular dominance plasticity. *J. Neurobiol.* 41, 83-91 (1999).

Wu, L. et al. CPEB-mediated cytoplasmic polyadenylation and the regulation of experience-dependent translation of -CaMKII mRNA. *Neuron* 21, 1129-1139 (1998).

Chung, H. J., Xia, J., Scannevin, R. H., Zhang, X. & Huganir, R. L. Phosphorylation of the AMPA receptor subunit GluR2 differentially regulates its interaction with PDZ domain-containing proteins. *J. Neurosci.* 20, 7258-7267 (2000).

Example 3

Fragile X Mental Retardation

Fragile X syndrome is a prevalent form of inherited mental retardation, occurring with a frequency of 1 in 4000 males and 1 in 8000 females. The syndrome is also characterized by developmental delay, hyperactivity, attention deficit disorder, and autistic-like behaviors (Jin, P., et al., *Hum Mol Genet*, 9:901-8, (2000)). There is no effective treatment for Fragile X syndrome.

The syndrome is typically caused by a repeat expansion mutation in the FMR1 (Fragile X Mental Retardation 1) gene that encodes FMRP (Fragile X Mental Retardation Protein). FMRP associates with translating polyribosomes and a subset of brain mRNAs, and functions as a regulator of protein synthesis (Feng, Y., et al., *Mol Cell* 1:109-18 (1997); Brown, V., et al., *Cell* 107:477-87 (2001); Darnell, J. C., et al., *Cell* 107:489-99 (2001); Zhang, Y. Q., et al., *Cell* 107:591-603 (2001)). Polyribosomes, FMR1 mRNA, and FMRP are present in dendritic spines, the major site of synaptic transmission on cortical neurons (Weiler, I. J., et al., *Am J Med Genet* 83:248-52 (1999)). The Fmr1 null mutant (Fmr1-KO (knock out)) mouse, which has a behavioral phenotype consistent with Fragile X syndrome, was employed to determine the involvement of FMRP in synaptic plasticity. Protein synthesis-dependent, late-phase long-term synaptic potentiation (LTP) is unaffected in the hippocampus of mutant mice (Godfraind, J. M., et al., *Am J Med Genet* 64:246-251 (1996); Paradee, W., et al., *Neuroscience* 94:185-92 (1999)).

Local, synaptic control of protein synthesis is required for stable expression of a second form of hippocampal synaptic modification: long-term synaptic depression (LTD). As shown herein, LTD is triggered by activation of Group I metabotropic glutamate receptors (mGluRs). FMRP may be involved in this form of synaptic plasticity since FMRP is one of the proteins synthesized in response to mGluR activation (Weiler, I. J., et al., *Am J Med Genet* 83:248-52 (1999)).

As shown herein, mGluR-dependent LTD (mGluR-LTD), a protein synthesis-dependent form of synaptic plasticity, is significantly activated in the hippocampus of Fmr1-KO mice. FMRP normally functions as a negative regulator of translation (Zhang, Y. Q., et al., *Cell* 107:591-603 (2001); Laggerbauer, B., et al., *Hum Mol Genet* 10:329-38 (2001); Li, Z., et al., *Nucleic Acids Res* 29:2276-83 (2001)). FMRP has an important functional role in regulating activity-dependent synaptic plasticity. Thus, exaggerated LTD and/or mGluR function may be responsible for aspects of the behavioral phenotype in Fragile X syndrome, and antagonists of Group I mGluRs (e.g., mGluR5, mGluR1) can be employed as therapeutic agents in the treatment of Fragile X syndrome.

Materials and Methods

Hippocampal slices were prepared from postnatal day (P) 21-30, C57BL/6 congenic Fmr1-KO mice and their wildtype littermates as previously described. Briefly, slices were collected in ice-cold dissection buffer containing 212 mM sucrose; 2.6 mM KCl; 1.25 mM $NaH_2PO_4$; 26 mM $NaHCO_3$; 5 mM $MgCl_2$; 0.5 mM $CaCl_2$; and 10 mM dextrose. The CA3 position of the hippocampus was removed immediately after sectioning. Slices recovered were placed for 1-5 hr at 30° C. in artificial cerebrospinal fluid (ACSF) containing 124 mM NaCl; 5 mM KCl; 1.25 mM $NaH_2PO_4$; 26 mM $NaHCO_3$; 1 mM $MgCl_2$; 2 mM $CaCl_2$; 10 mM dextrose, saturated with 95% $O_2$, 5% $CO_2$. For recording of field potentials, slices were placed in a submersion recording chamber and perfused with 30° C. ACSF at a rate of 2 ml/min.

Field potentials (FPs) were recorded with extracellular recording electrodes filled with ACSF and placed in the stratum radiatum of area CA1. Synaptic responses were evoked by a 200 μsec current pulse to Schaffer collateral axons with a concentric bipolar tungsten stimulating electrode. Stable baseline responses were collected every 30 sec using a stimulation intensity (10-30 μA) yielding 50-60% of the maximal response. mGluR-LTD was induced in the presence of the N-methyl-D-aspartate (NMDA) receptor (NMDAR) antagonist D-(−)-2-amino-5-phosphono-pentanoic acid (D-APV) (50 M) using paired-pulse low frequency stimulation (PP-LFS) consisting of 900 pairs of stimuli (50 msec interstimulus interval) delivered at 1 Hz. NMDAR-LTD was induced using 900 single pulses delivered at 1 Hz (Dudek, S. M., et al., *Proc Natl Acad Sci USA* 89:4363-7 (1992)).

Waveforms were filtered at 2 kHz, acquired and digitized at 10 kHz on a PC using Experimenter's Workbench (DataWave Systems, Boulder, Colo.). The group data were analyzed as follows: (1) the initial slope of the FP for each experiment was expressed as percentages of the pre-conditioning or 3,5-dehydroxyphenylglycine (DHPG) baseline average, and (2) the time scale in each experiment was converted to time from the onset of pre-conditioning or DHPG baseline average. All experiments were performed blind to the genotype of the mice, determined after analysis of individual experiments. After genotyping, the time-matched, normalized data were averaged across experiments and expressed in the text and figures as the means (±SEM). Significant differences between groups were determined using an independent t-test and Komolgarov-Smirnov test.

R,S-DHPG ((R,S)-3,5-dihydroxyphenylglycine) and APV were purchased from Tocris (St. Louis, Mo.). All other chemicals were purchased from Sigma Chemical Co. (St Louis, Mo.). DHPG was prepared as a 100× stock in $H_2O$, aliquoted and stored at −20° C. Fresh stocks were made once a week. A 10× stock of APV was prepared in ACSF and stored at 4° C. The stocks were diluted in ACSF to achieve their final concentrations.

Results

Normal Synaptic Transmission in Fmr1-KO Mice

Hippocampal slices were prepared from postnatal day 21-30, C57BL/6 congenic Fmr1-KO mice and their wildtype littermates. Excitatory synaptic field potentials evoked by stimulation of the Schaffer collaterals were recorded extracellularly from the stratum radiatum of area CA1. In all cases, the experimenters were blind to the genotype.

Previous studies have examined the properties of transmission at Schaffer collateral synapses in the CA1 region of hippocampus of these mutant mice. In terms of basal transmission, excitability, paired-pulse facilitation, early phase LTP elicited with 100 Hz stimulation, and late-phase (protein synthesis-dependent) LTP induced with theta-burst stimulation, Fmr1-KO mice were indistinguishable from wild-type (WT) littermates (Godfraind, J. M., et al., *Am J Med Genet* 64:246-51 (1996); Paradee, W., et al., *Neuroscience* 94:185-92 (1999)). Thus, the excitatory synaptic transmission mediated by AMPA and NMDA receptors, and the state of inhibition, are not appreciably affected by the absence of FMRP. Field potential amplitudes, in response to increasing stimulus current, were not different between Fmr1-KO and wildtype littermates ($F(1,350)=0.358$, $P>0.5$), the maximum amplitude of field potentials from Fmr1-KO mice (1.73±0.19 mV; n=39 slices from 17 mice) was not different from wildtype (WT; 1.63±0.16 mV; n=36 slices from 18 mice; p=0.36), and the stimulus currents used to evoke baseline responses were not different between groups (Fmr1-KO 22±1 mA; WT23±2 mA).

mGluR-LTD Induced by Synaptic Stimulation is Enhanced in Fmr1-KO Mice

As shown herein, paired-pulse stimulation repeated at 1 Hz for 15 minutes (PP-LFS) induces LTD that is independent of NMDA receptors, and requires activation of Group I mGluRs and the rapid translation of preexisting mRNA. The consequences of PP-LFS hippocampal in slices from KO (knock out) and WT (wild type) animals was also determined herein.

PP-LFS (delivered in the presence of 50 μM D-2-amino-5-phosphonovalerate (APV) to block NMDA receptors) produced a significant LTD in WT mice (93±3% 60 min following PP-LFS; n=21 slices from 10 mice; FIGS. 10A, 10B and 10C).

The magnitude of LTD in these experiments is considerably less than previously reported in rats as described above, which may be due to the species and strain of mice employed. The magnitude of LTD induced with PP-LFS was significantly increased in slices prepared from KO animals (82±3%; n=18 slices from 8 mice; different from WT at p<0.004; t-test). The difference was initially observed about 15 minutes after the tetanus and there was no indication that responses during or immediately after the PP-LFS were different in KO and WT animals (FIGS. 10A and 10B). FIG. 10A depicts the average time course of the change in FPs following PP-LFS. LTD in KO animals measured 82±3% of pre-PP-LFS baseline (n=18 slices from 8 mice; open circles) as compared to 93±2% in WT controls (n=21 slices from 10 mice; filled circles; different at p=0.004, t-test). FIG. 10B depicts representative FPs (2 min average) taken at the times indicated by the numbers on the graph. Scale bars: 1 mV, 5 msec (1,2) and 1 mV, 10 msec (PP-LFS).

The Kolmolgarov-Smirnov test on the cumulative probability distribution, showed that the distribution of depression values was different between KO and WT groups was significantly different (p<0.05; FIG. 10C). FIG. 10C depicts cumulative probability distributions of FP slope values (% of baseline), measured on hour after PP-LFS in individual slices from both KO and WT groups.

mGluR-LTD Induced by DHPG is Enhanced in Fmr1-KO Mice mGluR LTD can be induced by the selective-Group I mGluR agonist DHPG ((RS)-3,5-dihydroxyphenylglycine) which more uniformly affects synapses and circumvents the need for presynaptic activation. Dose-dependent induction of LTD following DHPG (50-100 μM, 5 min) occurs. As shown herein, activation of mGluR5 is required for induction, and protein synthesis is required for stable expression, of DHPG-LTD. LTD with PP-LFS and DHPG are mutually occluding, which may indicate they utilize the same saturable expression mechanism. DHPG was employed to induce plasticity to determine whether mGluR-LTD is increased in Fmr1-KO mice using an independent method.

As described above, experiments were performed in the presence of APV to eliminate the confound of NMDA receptor-dependent synaptic modifications. DHPG (100 μM, 5 min) induced a saturating level of LTD. The data show a significant enhancement of mGluR-LTD in slices from KO mice (FIGS. 11A, 11B and 11C).

DHPG application to slices from Fmr1-KO mice resulted in depression of FP slope values to 77±3% of pre-DHPG baseline (measured 60 min after DHPG application n=21 slices from 9 mice). In comparison, DHPG-induced LTD was 88±4% in WT mice (15 slices from 8 animals; p=0.02; FIGS. 11A, 11B). FIG. 11A depicts the average (±SEM) field potential (FP) slope values over the time course of the experiment. In Fmr1-KO animals, the response 60 min after treatment was depressed to 77±3% of pre-DHPG baseline (n=21 slices from 9 mice; open circles); in interleaved WT controls, the response was depressed to 88±4% of baseline (n=15 slices from 8 mice; filled circles; different at p=0.02; t-test). FIG. 11B depicts representative FPs (2 min average) taken at the times indicated by the numbers on the graph (Scale bar: 1 mV; 5 msec).

The Kolmolgarov-Smirnov test performed on the cumulative probability distribution confirmed the statistical significance of this difference (p<0.05; FIG. 11C). FIG. 11C depicts cumulative probability distributions of FP slope values (% of baseline), measured one hour after DHPG in individual hippocampal slices from both KO and WT groups.

Although the acute effect of DHPG on synaptic transmission also appeared to be slightly enhanced in Fmr1-KO slices, this difference was not statistically significant (maximal acute depression: WT: 36±4%, KO: 26±5% of pre-DHPG baseline values). Western blots of hippocampal homogenates also confirmed that mGluR5 levels are comparable in KO and WT mice.

NMDA Receptor-dependent LTD is Normal in Fmr1-KO Mice

Two forms of homosynaptic LTD coexist at CA3-CA1 synapses: mGluR-LTD and a form which is triggered by activation of NMDA receptors (NMDAR-LTD) (Oliet, S. H. et al., *Neuron* 18:969-82 (1997)). As shown herein, NMDAR-LTD in hippocampal slices is independent of mGluR activation and protein synthesis, and requires activation of postsynaptic protein phosphatases. To determine whether FMRP selectively regulates protein synthesis-dependent plasticity or LTD mechanisms in general NMDAR-LTD in Fmr1-KO mice was examined. NMDAR-LTD was elicited by delivering 900 single pulses at 1 Hz (Dudek, S. M., et al., *Proc Natl Acad Sci USA* 89:4363-7 (1992)). In contrast to mGluR-LTD, NMDAR-LTD was normal in Fmr1-KO mice (86±4%; 14 slices from 8 animals) as compared to WT littermates (84±4%; 12 slices from 4 animals; p=0.6; FIGS. 12A, 12B and 12C).

FIG. 12A depicts the average time course of the change in FPs following low-frequency stimulation (LFS). LTD in KO animals measured 86±4% of pre-LFS baseline (n=14 slices from 8 mice; open circles) as compared to 84±4% in wild-type controls (n=12 slices from 4 mice; filled circles; p=0.6, t-test). FIG. 12B depicts the representative FPs (2 min average) taken at the times indicated by the numbers on the graph (Scale bar: 1 mV, 10 msec). FIG. 12C depicts the cumulative probability distributions of FP slope values (% of baseline), measured on hour after LFS in individual slices from both KO and WT groups.

The data described herein show that FMRP specifically regulates mGluR- and protein synthesis-dependent synaptic plasticity. As shown herein, using two distinct induction protocols, mGluR-dependent LTD is significantly increased in the hippocampus of animals lacking FMRP. FMRP regulates LTD downstream of the mGluRs, likely at the level of mRNA translation. Since Fragile X syndrome is related to exaggerated mGluR-dependent synaptic plasticity, drugs that inhibit Group I mGluRs and/or LTD can be used for the treatment of neurological disorders including Fragile X syndrome.

Discussion

Involvement of FMRP in the Regulation of LTD

Activation of postsynaptic Group I mGluRs (e.g., mGluR5 and mGluR1), by the selective agonist (e.g., DHPG) or by synaptically released glutamate, triggers LTD at Schaffer collateral synapses in area CA1 of the hippocampus. One expression mechanism for the LTD of synaptic transmission is the internalization of AMPA and NMDA receptors (Snyder, E. M., et al., *Nat Neurosci* 4:1079-85 (2001); Xiao, M. Y., et al., *Neuropharmacology* 41:664-71 (2001)). Both synaptic depression and glutamate receptor internalization initiated by mGluR activation without new protein synthesis, but the stable expression of the change fails to occur when mRNA translation (but not transcription) is inhibited (see above). The critical site of protein synthesis is the postsynaptic dendrite.

An mRNA that is translated in response to postsynaptic Group I mGluR activation encodes FMRP (Weiler, I. J., et al., *Am J Med Genet* 83:248-52 (1999)). Thus, the data described herein shows that the mGluR-dependent synthesis of FMRP plays a role in the stabilization of LTD. FMRP can function as a negative regulator of mRNA translation (Zhang, Y. Q., et al., *Cell* 107:591-603 (2001); Laggerbauer, B., et al., *Hum Mol Genet* 10:329-38 (2001); Li, Z., et al., *Nucleic Acids Res* 29:2276-83 (2001)). FMRP normally serves to limit expression of LTD by inhibiting mGluR-dependent translation of other synaptic mRNAs (FIG. 13).

As shown in FIG. 13, activation of mGluR5 stimulates the internalization of AMPA receptors (AMPAR) and NMDA receptors. The stable expression of this modification requires protein synthesis, which may be negatively regulated by FMRP synthesized in response to mGluR activation. Therefore, in the absence of FMRP, LTD magnitude is increased.

An mRNA that is negatively regulated by FMRP encodes the microtubule associated protein MAP1b, which has been shown in *Drosophila* to regulate synaptic structure and function (Zhang, Y. Q., et al., *Cell* 107:591-603 (2001)). An increase of MAP1b mRNA on polyribosomes in cells derived from patients with Fragile X syndrome, has recently been reported.

In addition to LTD triggered by activation of Group I mGluRs, homosynaptic LTD can be is induced by activating NMDA receptors (Bear, M. F., et al., *Annu Rev Neurosci* 19:437-62 (1996)). In hippocampal slices, expression of NMDAR-mediated LTD is not protein synthesis dependent for at least 1 hr and does not occlude mGluR-mediated LTD.

Normal NMDAR-LTD in the Fmr1-KO mice shows that these forms of LTD utilize distinct mechanisms. Another form of NMDAR-dependent plasticity, LTP, is also unaffected in Fmr1 knockout mice (Godfraind, J. M., et al., *Am J Med Genet* 64:246-51 (1996); Paradee, W., et al., *Neuroscience* 94:185-92 (1999)). The data described herein show that FMRP may be selectively involved in synaptic modifications that are triggered in response to mGluR-stimulated protein synthesis.

Role of LTD and FMRP in Cortical Development

LTD and LTP may normally work in concert to fine-tune patterns of synaptic connectivity during development (Bear, M. F., et al., *Science* 237:42-8 (1987); Bear, M. F., et al., *J Neurobiol* 41:83-91 (1999)) and to store memories in the adult brain (Bear, M. F., *Proc Natl Acad Sci USA* 93:13453-9 (1996)). As shown herein, activation of mGluRs in cultured hippocampal neurons is a long-term decrease in the surface expression of the ionotropic glutamate receptors that mediate synaptic transmission, possibly as a prelude to synapse elimination (Snyder, E. M., et al., *Nat Neurosci* 4:1079-85 (2001)). Thus, in the absence of FMRP, enhanced LTD may interfere with the establishment and maintenance of strong synapses required for normal brain function.

Dendritic spine development is slowed in the cerebral cortex of Fmr1-KO mice (Nimchinsky, E. A., et al., *J Neurosci* 21:5139-46 (2001)). Dendritic spines are the major targets of glutamatergic synapses in the cortex. Synapses are formed during development when long, thin protospines emitted by pyramidal cell dendrites make contact with nearby axons (Dailey, M. E., et al., *J Neurosci* 16:2983-94 (1996)). As the synapse stabilizes, the spines shorten and become fatter. An increased-percentage of long, thin dendritic processes, reminiscent of protospines, is a characteristic feature of cortical neurons in FMRP-deficient mice (Nimchinsky, E. A., et al., *J Neurosci* 21:5139-46 (2001); Comery, T. A., et al., *Proc Natl Acad Sci USA* 94:5401-4 (1997)) and affected humans (Hinton, V. J., et al., *Am J Med Genet* 41:289-94 (1991); Irwin, S. A., et al., *Am J Med Genet* 98:161-7 (2001)). An underlying defect may enhance activity- and mGluR-dependent synapse turnover, abnormally prolonging a state in which neurons are actively seeking new synaptic input. Hippocampal neurons in culture express significantly longer, thinner spines following DHPG treatment, which requires protein synthesis (Vanderklish, P. W., et al., *Proc Natl Acad Sci USA* 99:1639-44 (2002)).

Treatment of Fragile X Syndrome

The association of Group I mGluRs and activity-dependent protein synthesis is not restricted to early postnatal development, the cerebral cortex, or LTD. mGluR- and protein synthesis-dependent LTD can be elicited in hippocampus from mature animals, where it may contribute to memory storage (Zheng, H., et al., *Cell* 107:617-29 (2001)), particularly during novel or stressful situations (Bear, M. F., *Proc Natl Acad Sci USA* 96:9457-8 (1999); Braunewell, K. H., et al., *Rev Neurosci* 12:121-40 (2001)). LTD in the cerebellum, which depends on Group I mGluRs, may contribute to learning motor reflexes (Bear, M. F., et al., In "*Synapses*," eds. Cowan, W. M., Sudhoff, et al., The Johns Hopkins University Press, Baltimore, pp. 455-517 (2001)), requires rapid translation of mRNA (Karachot, L., et al., *J Neurophysiol* 86:280-9 (2001)). mGluR-triggered protein synthesis in the hippocampus can reduce the threshold for synaptic potentiation (Raymond, C. R., et al., *J Neurosci* 20:969-76 (2000)) and trigger epileptiform activity (Merlin, L. R., et al., *J Neurophysiol* 80:989-93 (1998); Wong, R. K., et al., *Adv Neurol* 79:685-98 (1999)). FMRP may normally function as a negative feedback regulator of these physiological processes. The prominent features of Fragile X syndrome also include heightened responses to novelty, compulsions, and seizures.

The methods described herein can be used to treat these heightened responses to novelty, compulsions, seizures, anxiety and epilepsy in a human with a neurological disorder or condition, in particular a human with Fragile X syndrome.

Fragile X mental retardation may be a consequence of increased mGluR-dependent protein synthesis and/or LTD in the brain, both during early postnatal development and in adulthood. LTD magnitude increases with increasing activation of mGluR5. Titration of a competitive antagonist may produce a graded reduction in mGluR- and protein synthesis-dependent response. These data show that Group I mGlu5 can be useful to treat neurological disorders including Fragile X syndrome.

All patents, publications, and other references cited above are hereby incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a subject, comprising the step of administering a Group I mGluR antagonist to a subject having autism wherein the autism is thereby treated.

2. The method of claim 1, wherein the subject has fragile X syndrome.

3. The method of claim 1, wherein the subject has a disorder of at least one member selected from the group consisting of a seizure disorder or an anxiety disorder.

4. The method of claim 3, wherein the seizure disorder is epilepsy.

5. The method of claim 2, wherein the subject has a disorder of at least one member selected from the group consisting of a seizure disorder or an anxiety disorder.

6. The method of claim 5, wherein the seizure disorder is epilepsy.

7. The method of claim 1, wherein the Group I mGluR antagonist has an ED50 for antagonism of a Group I receptor at least 10 times less than the ED50 for antagonism of a Group II or a Group III receptor.

8. The method of claim 1, wherein the Group I mGluR antagonist is a mGluR5 antagonist.

9. The method of claim 1, wherein the Group I mGluR antagonist has an ED50 for mGluR5 antagonism at least 10 times less than the ED50 for mGluR1 antagonism.

10. The method of claim 1, wherein the Group I mGluR antagonist has an ED50 for mGluR5 antagonism at least 100 times less than the ED50 for antagonism of ionotropic glutamate receptors.

11. The method of claim 1, wherein the subject is a human subject.

12. The method of claim 1, wherein the Group I mGluR antagonist is a mGluR1 antagonist.

13. The method of claim 1, wherein the Group I mGluR antagonist is administered in a dose ranging from about 10 to about 1000 mg/kg body weight/day.

14. The method of claim 1, wherein the Group I mGluR antagonist has an ED50 of 1 µM or less.

15. The method of claim 14, wherein the Group I mGluR antagonist has an ED50 of 100 nM or less.

16. The method of claim 1, wherein the mGluR antagonist has a therapeutic index of 10 or greater.

17. The method of claim 16, wherein the Group I mGluR antagonist has a therapeutic index of 100 or greater.

18. The method of claim 1, wherein the Group I mGluR antagonist binds to a Group I mGluR.

19. The method of claim 1, wherein the Group I mGluR antagonist interacts with an intracellular G protein involved in a Group I mGluR signal transduction pathway.

20. A method of treating a subject, comprising the step of administering an mGluR5 antagonist to a subject having autism wherein the autism is thereby treated.

21. The method of claim 20, wherein the subject has fragile X syndrome.

22. The method of claim 20, wherein the subject has a disorder of at least one member selected from the group consisting of a seizure disorder or an anxiety disorder.

23. The method of claim 22, wherein the seizure disorder is epilepsy.

24. The method of claim 21, wherein the subject has a disorder of at least one member selected from the group consisting of a seizure disorder or an anxiety disorder.

25. The method of claim 24, wherein the seizure disorder is epilepsy.

26. The method of claim 20, wherein the subject is a human subject.

27. The method of claim 20, wherein the Group I mGluR antagonist binds to a Group I mGluR.

28. The method of claim 20, wherein the Group I mGluR antagonist interacts with an intracellular G protein involved in a Group I mGluR signal transduction pathway.

29. A method of treating a subject, comprising the step of administering an mGluR1 antagonist to a subject having autism wherein the autism is thereby treated.

30. The method of claim 29, wherein the subject has fragile X syndrome.

31. The method of claim 29, wherein the subject has a disorder of at least one member selected from the group consisting of a seizure disorder or an anxiety disorder.

32. The method of claim 31, wherein the seizure disorder is epilepsy.

33. The method of claim 30, wherein the subject has a disorder of at least one member selected from the group consisting of a seizure disorder or an anxiety disorder.

34. The method of claim 33, wherein the seizure disorder is epilepsy.

35. The method of claim 29, wherein the subject is a human subject.

36. The method of claim 29, wherein the Group I mGluR antagonist binds to a Group I mGluR.

37. The method of claim 29, wherein the Group I mGluR antagonist interacts with an intracellular G protein involved in a Group I mGluR signal transduction pathway.

38. A method of treating a subject, comprising the step of administering an effective amount of a Group I mGluR antagonist to a subject having autism, wherein the Group I mGluR antagonist is selected from the group consisting of (E)-6-methyl-2-styryl-pyridine (SIB 1893), 6-methyl-2-(phenylazo)-3-pyridinol, α-methyl-4-carboxyphenylglycine (MCPG) and 2-methyl-6-(phenylethynyl)-pyridine (MPEP) where the autism is thereby treated.

39. The method of claim 38, wherein the subject has fragile X syndrome.

40. The method of claim 38, wherein the subject is a human subject.

41. A method of treating a subject comprising the step of administering an effective amount of a Group I mGluR antagonist to a subject having autism and fragile X syndrome where the autism is thereby treated.

42. The method of claim 41, wherein the subject has at least one disorder selected from the group consisting of a seizure disorder and an anxiety disorder.

43. The method of claim 42, wherein the seizure disorder is epilepsy.

44. The method of claim 41, wherein the mGluR antagonist is a mGluR5 antagonist.

45. The method of claim 41, wherein the mGluR antagonist is a mGluR1 antagonist.

46. The method of claim 41, wherein the subject is a human subject.

47. The method of claim 41, wherein the Group I mGluR antagonist binds to a Group I mGluR.

48. The method of claim 41, wherein the Group I mGluR antagonist interacts with an intracellular G protein involved in a Group I mGluR signal transduction pathway.

* * * * *

UNITED STATES PATENT AND TRADEMARK OFFICE
CERTIFICATE OF CORRECTION

| | | |
|---|---|---|
| PATENT NO. | : 7,648,993 B2 | Page 1 of 1 |
| APPLICATION NO. | : 11/015328 | |
| DATED | : January 19, 2010 | |
| INVENTOR(S) | : Mark F. Bear, Kimberly M. Huber and Stephen T. Warren | |

It is certified that error appears in the above-identified patent and that said Letters Patent is hereby corrected as shown below:

Title page 1, Item (75), delete "Bristol, RI" and insert --Boston, MA--;

In Claim 38, line 15, delete "where" and insert --wherein--;

In Claim 41, line 23, delete "where" and insert --wherein--;

Signed and Sealed this
Twenty-fourth Day of April, 2012

David J. Kappos
*Director of the United States Patent and Trademark Office*

UNITED STATES PATENT AND TRADEMARK OFFICE
CERTIFICATE OF CORRECTION

PATENT NO. : 7,648,993 B2  
APPLICATION NO. : 11/015328  
DATED : January 19, 2010  
INVENTOR(S) : Mark F. Bear, Kimberly M. Huber and Stephen T. Warren It is certified that error appears in the above-identified patent and that said Letters Patent is hereby corrected as shown below:

Title page 1, Item (75), delete "Bristol, RI" and insert --Boston, MA--;

In Claim 38, Column 58, line 15, delete "where" and insert --wherein--;

In Claim 41, Column 58, line 23, delete "where" and insert --wherein--;

This certificate supersedes the Certificate of Correction issued April 24, 2012.

Signed and Sealed this  
Fifteenth Day of May, 2012

David J. Kappos  
*Director of the United States Patent and Trademark Office*